(12) United States Patent
Bjerken

(10) Patent No.: US 7,615,064 B2
(45) Date of Patent: Nov. 10, 2009

(54) ENDOLUMENAL GASTRIC RING WITH SUSPENDED IMPEDING MEMBER

(75) Inventor: David Bjerken, Marietta, GA (US)

(73) Assignee: J.n Tailor Surgical, Inc., Marietta, GA (US)

( * ) Notice: Subject to any disclaimer, the term of this patent is extended or adjusted under 35 U.S.C. 154(b) by 159 days.

(21) Appl. No.: 11/878,775

(22) Filed: Jul. 26, 2007

(65) Prior Publication Data

US 2008/0027473 A1    Jan. 31, 2008

Related U.S. Application Data

(60) Provisional application No. 60/833,262, filed on Jul. 26, 2006, provisional application No. 60/848,644, filed on Oct. 3, 2006.

(51) Int. Cl.
*A61B 17/08* (2006.01)
*A61F 2/00* (2006.01)

(52) U.S. Cl. ......................................... 606/153; 600/37

(58) Field of Classification Search ......... 128/897–899; 600/32, 37; 604/8, 264, 909–910; 606/139, 606/144, 151, 153, 191–192, 197, 200, 213; 623/1.24, 1.26, 23.64–23.65, 23.7
See application file for complete search history.

(56) References Cited

U.S. PATENT DOCUMENTS

| | | | |
|---|---|---|---|
| 6,254,642 B1 | 7/2001 | Taylor | |
| 6,572,629 B2 | 6/2003 | Kalloo et al. | |
| 6,663,639 B1 | 12/2003 | Laufer et al. | |
| 6,675,809 B2 | 1/2004 | Stack et al. | |
| 6,773,441 B1 | 8/2004 | Laufer et al. | |
| 6,845,776 B2 | 1/2005 | Stack et al. | |
| 7,037,344 B2 | 5/2006 | Kagan et al. | |
| 7,097,650 B2 | 8/2006 | Weller et al. | |
| 7,111,627 B2 | 9/2006 | Stack et al. | |
| 7,121,283 B2 | 10/2006 | Stack et al. | |
| 7,146,984 B2 | 12/2006 | Stack et al. | |
| 7,152,607 B2 | 12/2006 | Stack et al. | |
| 7,172,613 B2 | 2/2007 | Wazne | |
| 7,175,638 B2 | 2/2007 | Gannoe et al. | |
| 7,175,660 B2 | 2/2007 | Cartledge et al. | |
| 7,201,757 B2 | 4/2007 | Knudson et al. | |
| 7,211,114 B2 | 5/2007 | Bessler et al. | |
| 7,220,237 B2 | 5/2007 | Gannoe et al. | |
| 7,220,266 B2 | 5/2007 | Gambale | |
| 7,220,284 B2 | 5/2007 | Kagan et al. | |
| 2004/0044357 A1* | 3/2004 | Gannoe et al. ............... 606/194 |

(Continued)

*Primary Examiner*—Anhtuan T Nguyen
*Assistant Examiner*—Ashley L. Cronin

(57) ABSTRACT

An implantable device including a supporting member, such as a ring, or series of rings, and an impeding member that is used to adjust the effective area of the created orifice after implantation. The rings may hold pleats of gastric tissue in place around their circumference to create a reinforced constriction within an organ. The rings may be attached to one another with folds or pleats of tissue held between them. If the organ is a stomach, the constriction is positioned such that a chamber of a predetermined volume is created proximal to the constriction, leaving a narrow opening or stoma to the remainder of the stomach's volume distal to the constriction. At least one of the rings is adapted to have an impeding member that may be endoscopically adjusted in order to alter the size of the effective orifice area of the opening or outlet. The occluding member may be a ball suspended by a suspension line connected to opposing sides of the supporting member.

11 Claims, 18 Drawing Sheets

U.S. PATENT DOCUMENTS

2004/0088008 A1    5/2004   Gannoe
2004/0092892 A1    5/2004   Kagan et al.
2005/0154374 A1*   7/2005   Hunter et al. ............ 604/890.1
2005/0177181 A1    8/2005   Kagan et al.
2007/0123994 A1    5/2007   Ortiz et al.

* cited by examiner

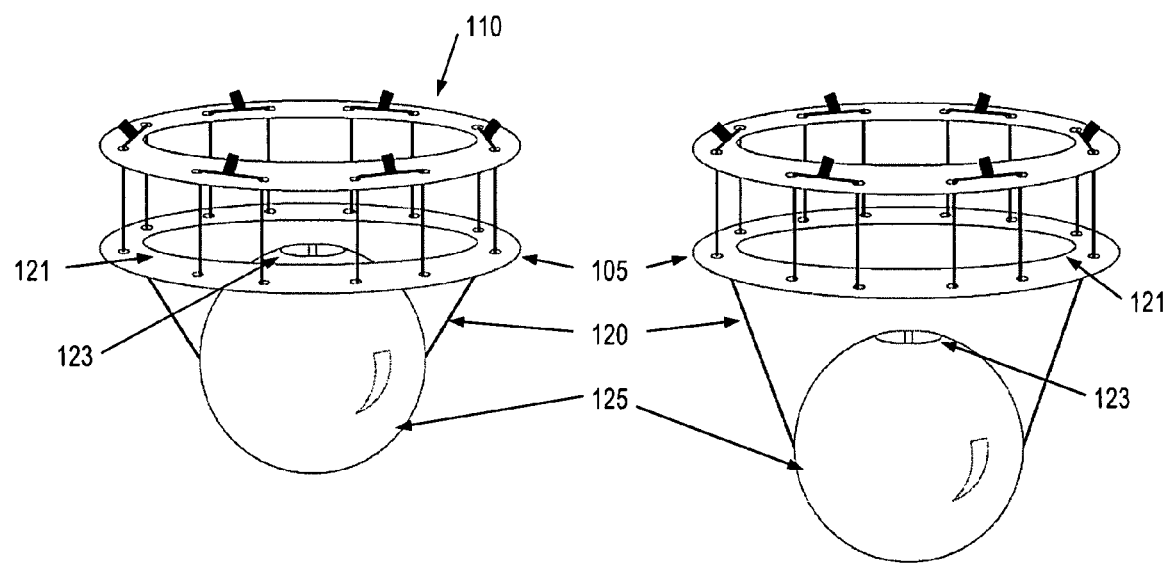
FIG. 7A     FIG. 7B
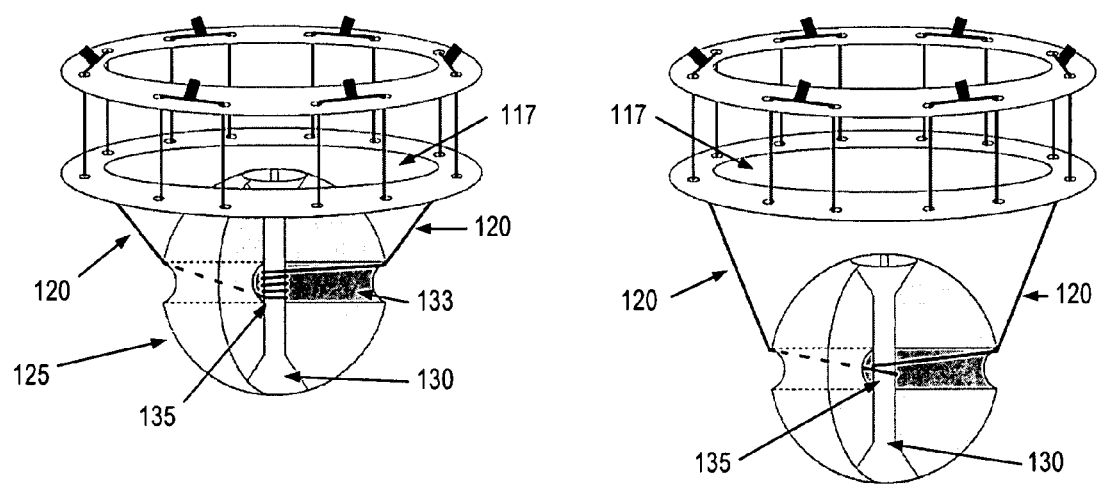
FIG. 8A     FIG. 8B

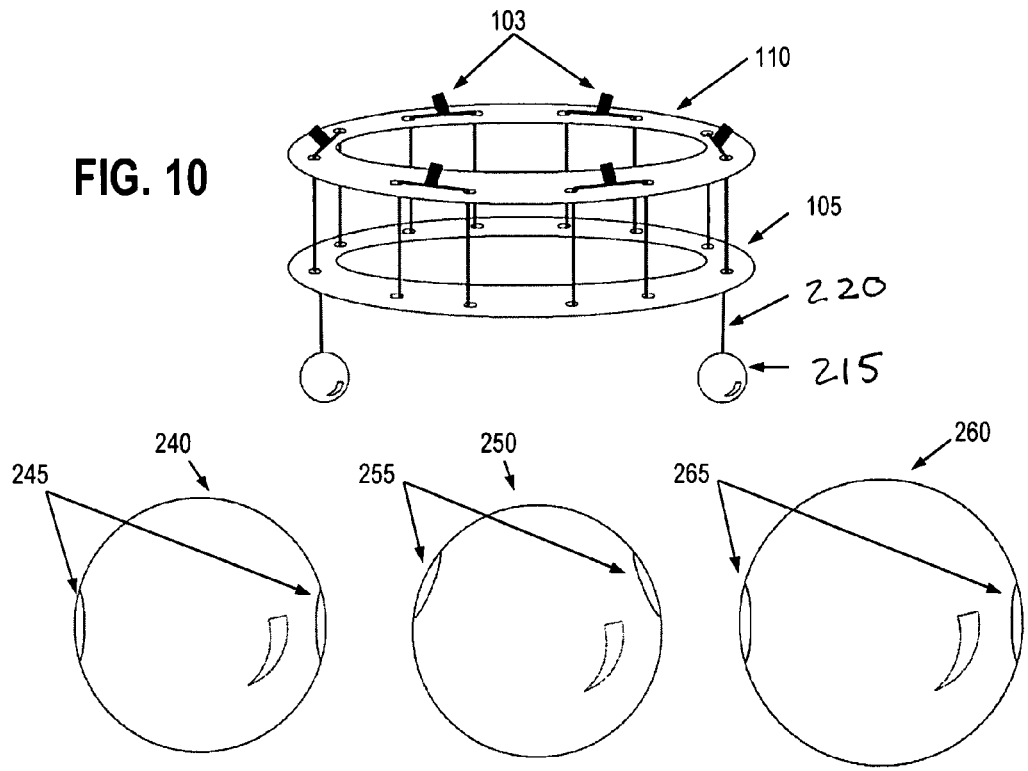
FIG. 10
FIG. 11A   FIG. 11B   FIG. 11C
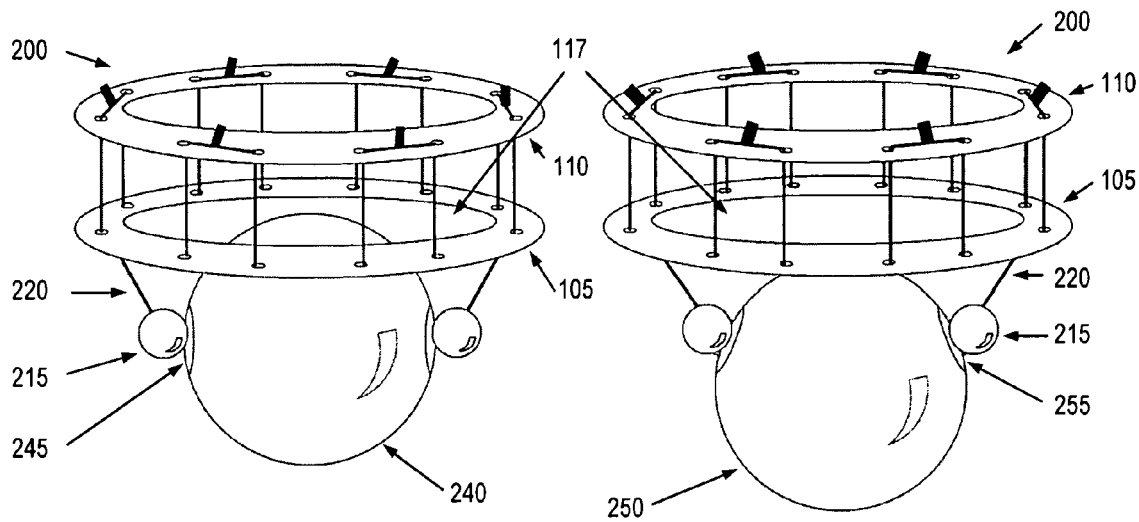
FIG. 12A   FIG. 12B

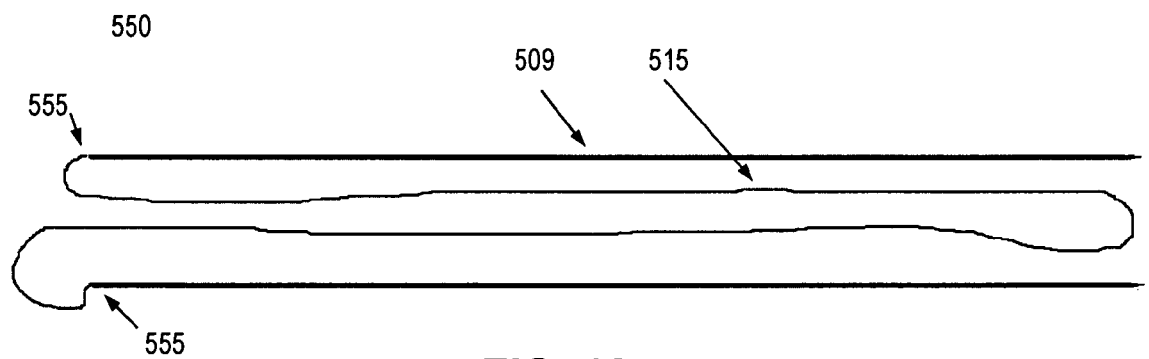
FIG. 18
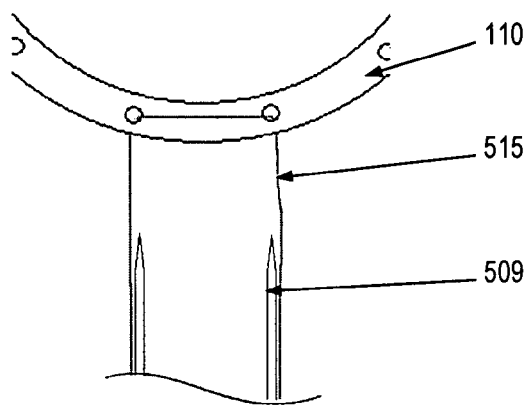
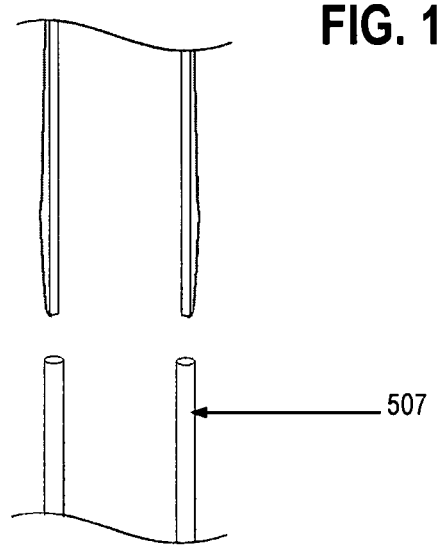
FIG. 19

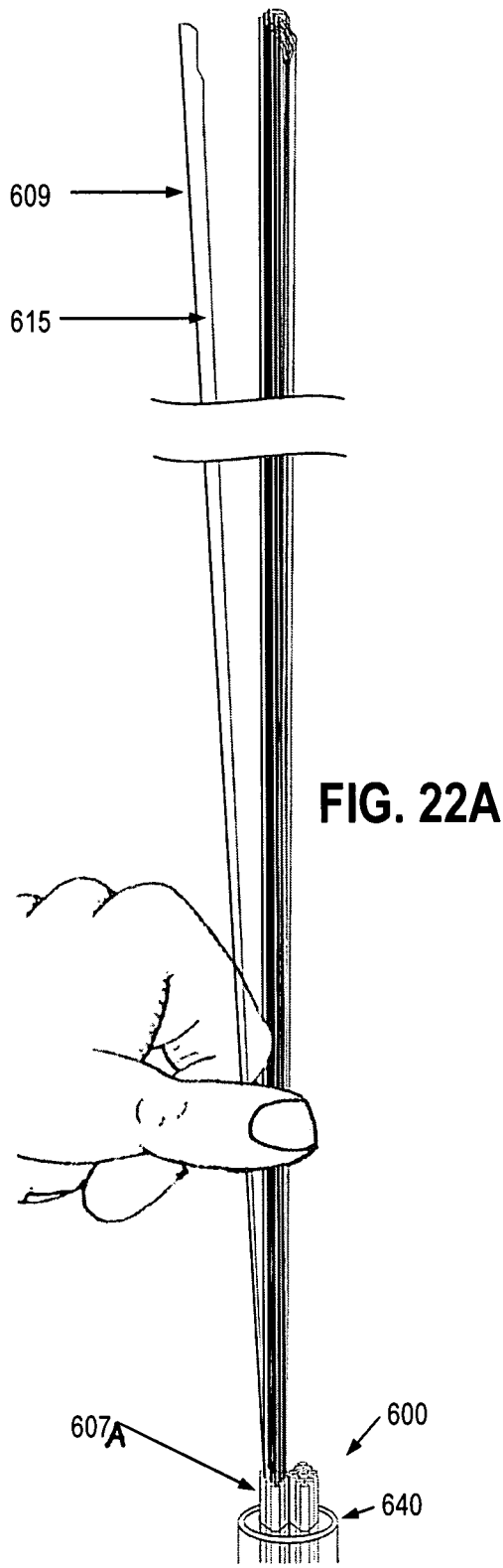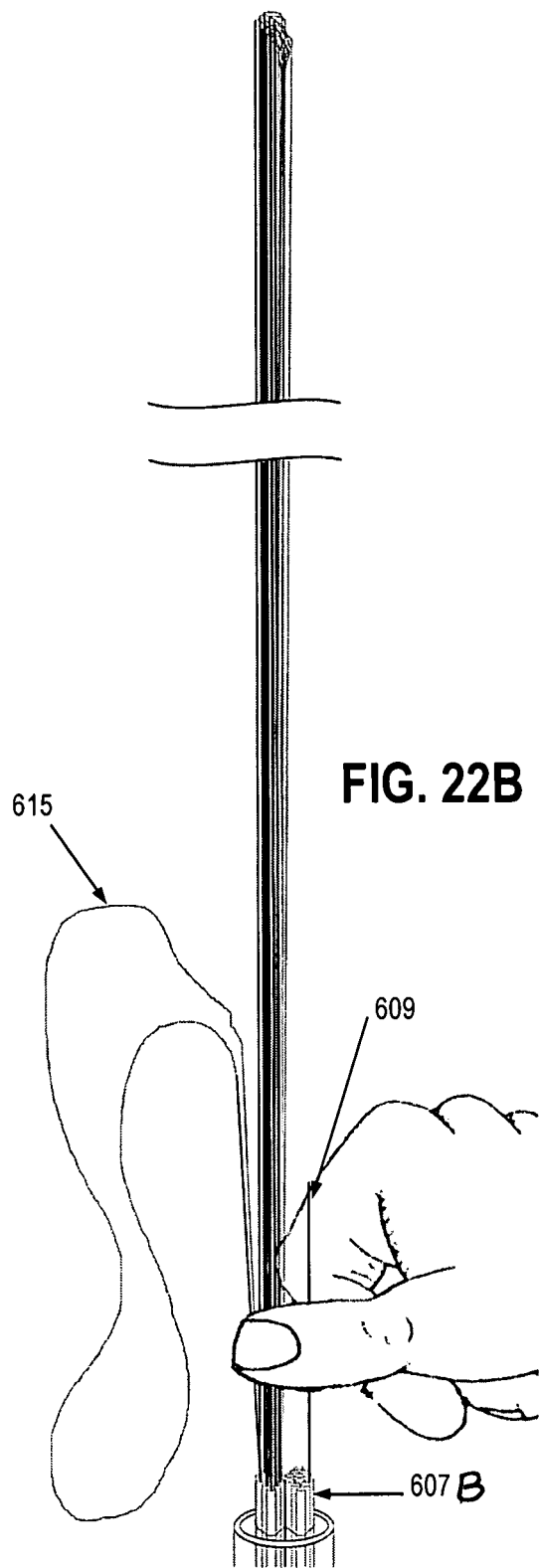

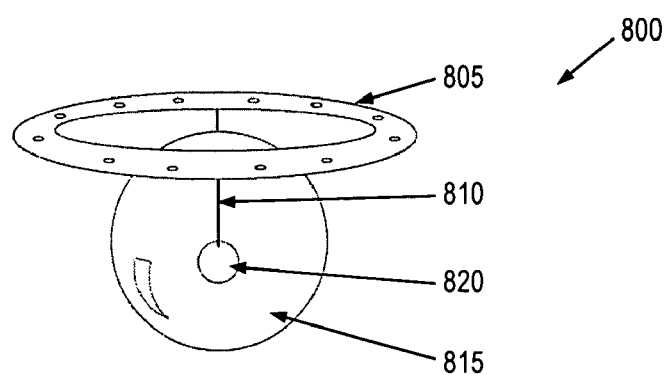
FIG. 24A
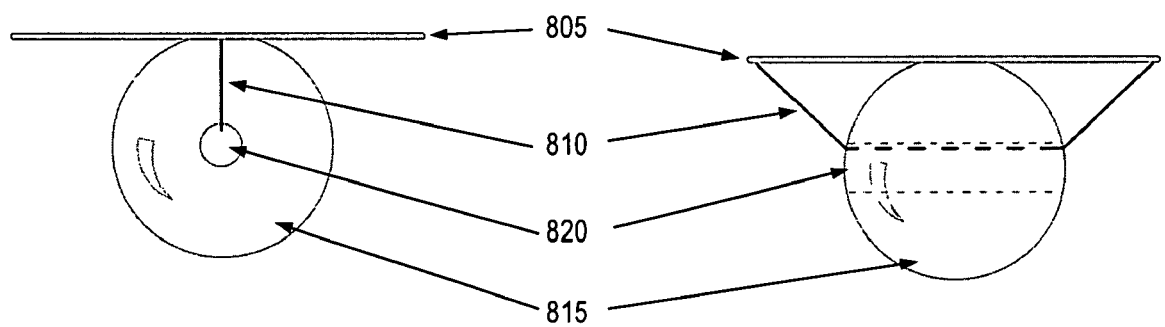
FIG. 24B  FIG. 24C

ENDOLUMENAL GASTRIC RING WITH SUSPENDED IMPEDING MEMBER

This application claims priority to Provisional Patent Application 60/833,262 filed on Jul. 26, 2006, and 60/848,644 filed on Oct. 3, 2006, which are hereby incorporated by reference for all purpose as if fully disclosed herein.

BACKGROUND OF THE INVENTION

1. Field of the Invention

The present invention generally relates to an endolumenal surgical device and procedure for the treatment and control of obesity. More particularly, the present invention relates to a gastric ring and suspended, impeding member for treatment and control of obesity.

2. Discussion of the Related Art

Various related art of surgical bariatric methods and devices have been disclosed to treat morbid obesity and to control weight gain. Some of those methods include gastric bypass and small bowel bypass surgery. Stapling of portions of the stomach has also been utilized, which includes both vertical and horizontal stapling and other variations that are intended to reduce the size of the stomach or make the stoma or stomach opening smaller.

These related art surgical procedures have several disadvantages. Stapling procedures may be unreliable and in some cases unsafe because the staples may come out or cause perforations and tears in the stomach wall. Further, the pouch or the outlet formed by the staples may become enlarged over time, thereby making the procedure useless. Further, gastric bypass surgery and stapling procedures do not generally allow for adjustability in the size of the stomach or stoma once the procedure has been completed. Adjustability of the stomach or stoma may be preferable after the patient's body or habits have changed.

Another related art device for weight control involves the use of a gastric band, which is placed around a portion of the stomach by open or laparoscopic surgery. The gastric band compresses the stomach and creates an outlet that is less than the normal interior diameter of the stomach. The constricted outlet restricts food intake into the lower digestive portion of the stomach. Gastric band procedures also have several disadvantages, such as band displacement or erosion of the band in the gastric lumen, to name a few. Such occurrences may cause pain and discomfort to the patient.

A further disadvantage of these related art method and devices is that they generally require complicated surgical procedures. Such procedures may include accessing and manipulating the patient's stomach and other internal organs via incisions. The invasiveness related to these surgical procedures can cause pain, prolonged recovery, complications, and in some cases may result in death. Moreover, the procedure can also be technically challenging for the surgeon, and cause great expense to the patient and the healthcare system in general.

Accordingly, what is needed is a device and method that serves to control weight gain and treat morbid obesity that may be implanted in the stomach in a non-invasive procedure, that allows adjustability, and that is reliable and safe for the person being treated.

SUMMARY OF THE INVENTION

The present disclosure describes an endolumenal gastric device with a suspended impeding member (e.g., a suspended impeding ball) that obviates one or more of the aforementioned problems due to limitations in the prior art.

Accordingly, one advantage of the invention is that it broadens a patient's options in choosing a non-invasive obesity treatment procedure.

Another advantage of the invention is that it provides a safer and more reliable surgical procedure to treat obesity.

Another advantage of the present invention is that it enables one to adjust the ability to ingest food material.

Yet another advantage of the present invention is that medication or other medical treatment may be administered via a suspended impeding ball.

Additional advantages of the invention will be set forth in the description that follows, and in part will be apparent from the description, or may be learned by practice of the invention. The advantages of the invention will be realized and attained by the structure pointed out in the written description and claims hereof as well as the appended drawings.

To achieve the aforementioned and other advantages, one exemplary embodiment involves an endolumenal implant. The implant comprises a supporting member that includes a central opening. The implant also comprises an impeding member that is, at least in part, suspended below the supporting member and substantially aligned with the central opening, wherein the vertical displacement of the impeding member relative to the central opening defines an effective orifice.

To achieve the aforementioned and other advantages, another exemplary embodiment involves an endolumenal implant that comprises a proximal ring and a distal ring, the proximal and distal rings defining a central opening. The endolumenal implant also comprises an impeding member suspended, at least in part, at a distance below the distal ring and substantially aligned with the central opening, wherein the central opening and the impeding member define an effective orifice through which material passes; and wherein the distance is adjusted to alter the effective orifice.

To achieve the aforementioned and other advantages, another aspect of the invention involves a method of modifying a stomach. The method involves introducing a first supporting member and a second supporting member into the stomach and securing the first and second supporting members to stomach tissue such that the stomach tissue is secured between the first and second supporting members. The method also involves suspending an impeding member, at least in part, below the first and second supporting members, wherein the first and second supporting members define a central opening and the impeding member is aligned with the central opening to form an effective orifice.

To achieve the aforementioned and other advantages, another aspect of the invention involves a method of modifying a stomach that involves inserting an endoscopic device through a patient's mouth and into the stomach, thereby introducing a distal ring into the stomach, wherein the endoscopic device is pre-loaded with needles, suture lines, and the distal ring, and wherein the suture lines are previously incorporated with the distal ring. The method further involves traversing through at least one fold in the stomach tissue, using the needles and suture lines. Still further, the method involves sliding the proximal ring along the suture lines; and coupling the proximal ring and the distal ring thereby securing the at least one fold in the stomach tissue therebetween.

To achieve the aforementioned and other advantages, still another aspect of the invention involves an apparatus for modifying a stomach. The apparatus comprises means for introducing a first supporting member and a second supporting member into the stomach, as well as means for securing the first and second supporting members to stomach tissue such that the stomach tissue is secured between the first and second supporting members. The apparatus also comprises means for suspending an impeding member, at least in part, below the first and second supporting members, wherein the first and second supporting members define a central opening and the impeding member is aligned with the central opening to form an effective orifice.

To achieve the aforementioned and other advantages, yet another aspect of the invention involves an apparatus for modifying a stomach, the apparatus comprising endoscopic device means for introducing a distal ring into the stomach through a patient's mouth, wherein the endoscopic device is pre-loaded with needles, suture lines, and the distal ring, and wherein the suture lines are previously incorporated with the distal ring. The apparatus also comprises means for traversing through at least one fold in the stomach tissue and means for introducing the proximal ring into the stomach along the suture lines and coupling the proximal ring and the distal ring, thereby securing the at least one fold in the stomach tissue therebetween.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the disclosure and are incorporated in and constitute a part of this specification, illustrate embodiments of the invention and together with the description serve to explain the principles of the invention.

FIG. 7A illustrates the impeding ball located a first exemplary distance from the rings;

FIG. 7B illustrates the impeding ball located a second exemplary distance from the rings;

FIG. 8A illustrates a cross sectional view of an impeding ball and an exemplary adjustment system located a first distance from the rings;

FIG. 8B illustrates a cross sectional view of an impeding ball and an exemplary adjustment system located a second distance from the rings;

FIG. 10 illustrates rings and suspension line according to another exemplary embodiment;

FIGS. 11A and 11B illustrate a perspective view of impeding balls having magnetic attachment points disposed in various locations according to another exemplary embodiment;

FIG. 11C illustrates a perspective view of an impeding ball of a larger size according to another exemplary embodiment;

FIG. 12A illustrates the exemplary rings of FIG. 10 coupled to the magnetic impeding ball of FIG. 11A;

FIG. 12B illustrates the exemplary rings of FIG. 10 coupled to the magnetic impeding ball of FIG. 11B;

FIG. 18 illustrates an exemplary double armed suture and needles with long wire needles;

FIG. 19 illustrates a sectional view of an exemplary double armed suture and needles cooperating with a distal ring according to the disclosure;

FIGS. 22A and 22B illustrate a perspective view of a needle being advanced through a cannula set of an exemplary suturing;

FIGS. 24A-24C illustrate alternate views of another exemplary embodiment of an impeding ball having a non-adjustable suspension line.

DETAILED DESCRIPTION OF THE ILLUSTRATED EMBODIMENTS

Figure 1:
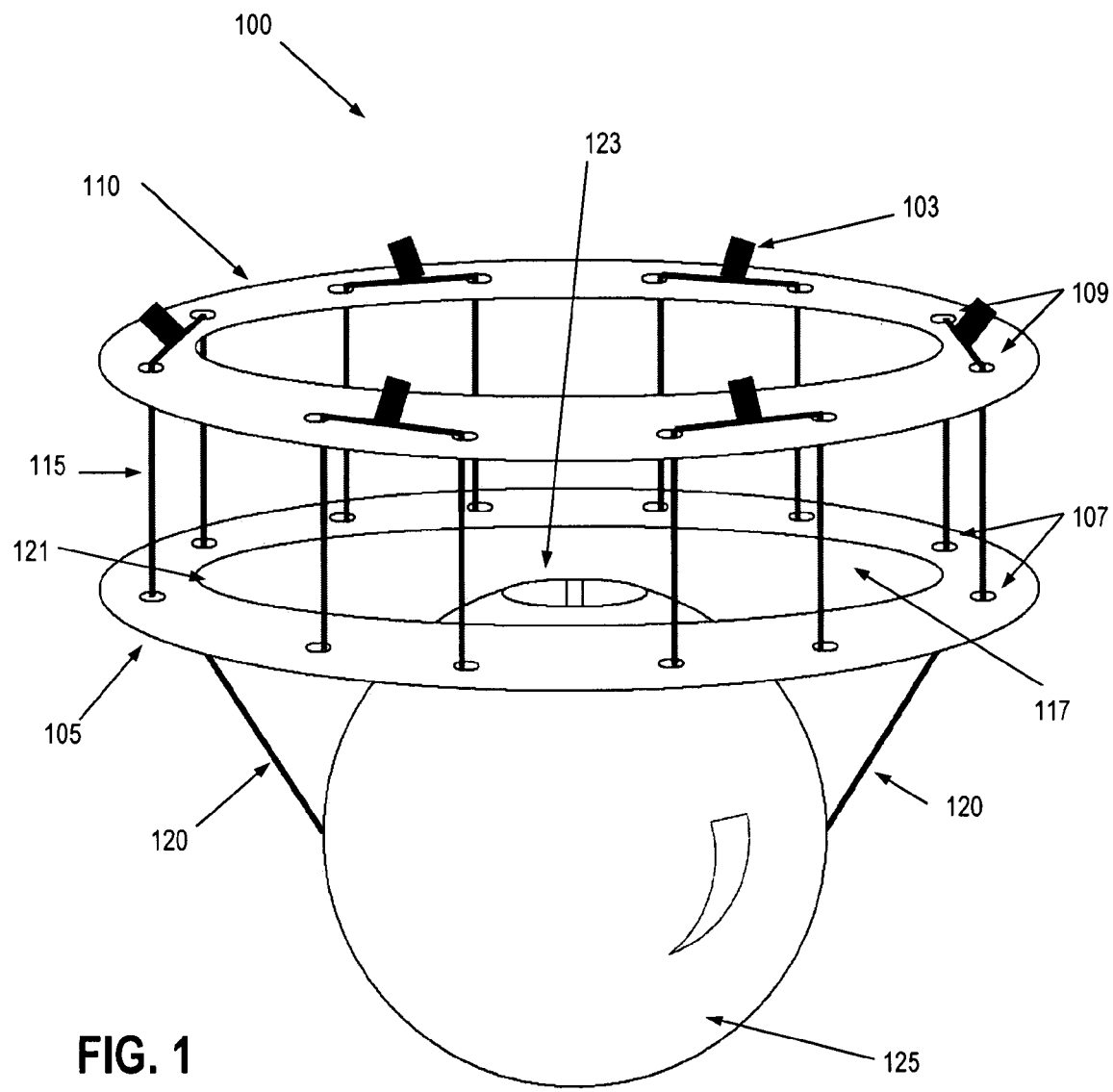
FIG. 1 illustrates an exemplary embodiment which includes endolumenal gastric rings with an impeding ball.

FIG. 1 illustrates an exemplary endolumenal implant 100 according to the disclosure. Endolumenal implant 100 includes a distal ring 105 that may be coupled to a proximal ring 110 by suture lines 115. Distal ring 105 and proximal ring 110 may thus be anchored to one another such that endolumenal tissue may be held therebetween in a desired configuration. Distal ring 105 and proximal ring 110 may have a plurality of first 107 and second 109 apertures, respectively, for attaching suture lines 115, or the like.

Distal ring 105 may incorporate one or more suspension lines 120 connected to distal ring 105. Suspension lines 120 may be connected at opposing sides of the circumference of the distal ring 105 or at arcuate intervals around distal ring 105 to stably suspend impeding ball 125. An impeding member, such as an impeding ball 125, may attach to distal ring 105 via suspension lines 120. Suspension lines 120 may run completely or partially through the ball, or directly attach to impeding ball 125. Alternatively suspension lines 120 may be releasably attached to impeding ball 125. Despite how impeding ball 125 is attached, it is envisioned that impeding ball 125 may be able to partially or freely rotate around suspension lines 120. Further, it will be appreciated that variations to the number and spacing of suspension lines 120 may be utilized depending on design constraints in order to ensure a reliable connection and that such variations are within the scope of the disclosure.

As illustrated in FIG. 1, impeding ball 125 may be suspended or slung across the central opening 117 of distal ring 105. One having skill in the art will appreciate that suspension lines 120 may be attached or incorporated with distal ring 105 and impeding ball 125 by means such as the use of a removable fastening device, epoxy, adhesive, integral molding, or any known means in the art that would ensure a durable and reliable connection. One having skill in the art will also appreciate that the various exemplary embodiments employ an impeding member that takes the form of a ball (i.e. spherical), however, other shaped are possible and considered within the scope of the invention.

Figure 2:
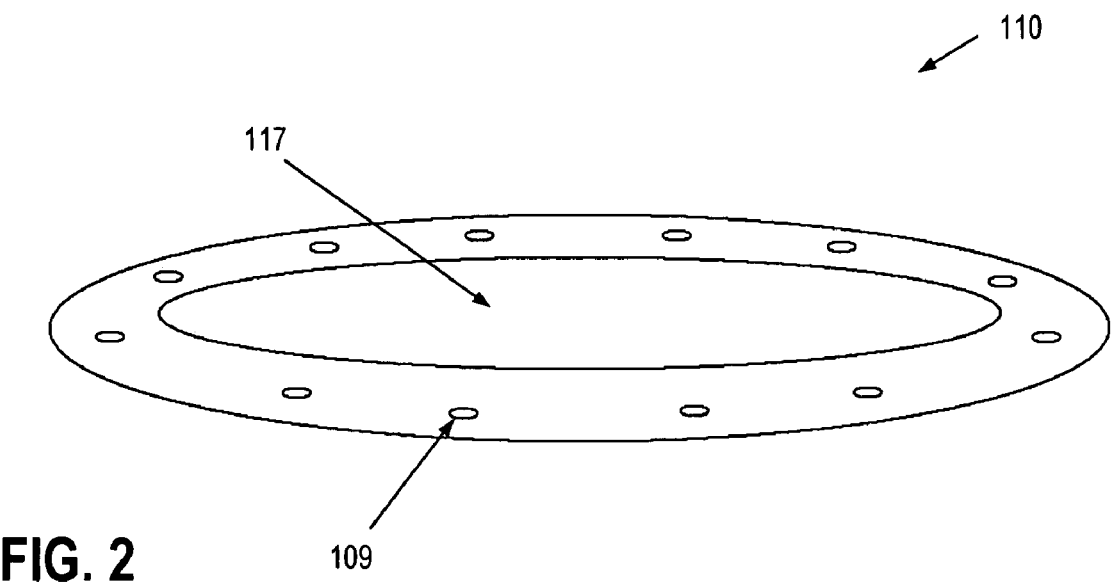
FIG. 2 illustrates a perspective view of an exemplary proximal ring.

FIG. 2 illustrates a perspective view of proximal ring 110. Proximal ring 110 may be circular, oval, triangular, or another noncircular shape. It will be appreciated that the distal ring 105 and proximal ring 110 may come in a variety of shapes so long as they include sufficient surface area to engage and effectively buttress endolumenal tissue therebetween in a manner that will radially distribute tension forces implied thereon, thereby resisting tearing of the endolumenal tissue. Further, distal ring 105 and proximal ring 110 may have a plurality of apertures 119 along their surface to allow for the passage of suture lines 115 (See FIG. 1) or other connecting material that may.

One having skill in the art will appreciate that various materials may be utilized for construction of proximal 110 and distal 105 rings in order to meet design requirements and biomedical restraints. Proximal 110 and distal 105 rings may be made of a rigid material, a semi-rigid material, or a non-rigid. Preferably, proximal ring 110 and distal ring 105 may be made of an elastic, bendable, or otherwise resilient material. Materials that are may be used and within the scope of the disclosure include metal, plastic, fabric, elastomers, or composite materials.

Proximal ring 110 may have substantially the same circumference as distal ring 105. It will be appreciated that the diameter of proximal ring 110 and distal ring 105 may vary in size depending upon the application, such as size or age of patient, and the endolumenal passage being treated, and that such variations are within the scope of the disclosure. For example, proximal 110 and distal 105 rings may have an internal diameter from 0.5" to 2.5".

Figure 3:
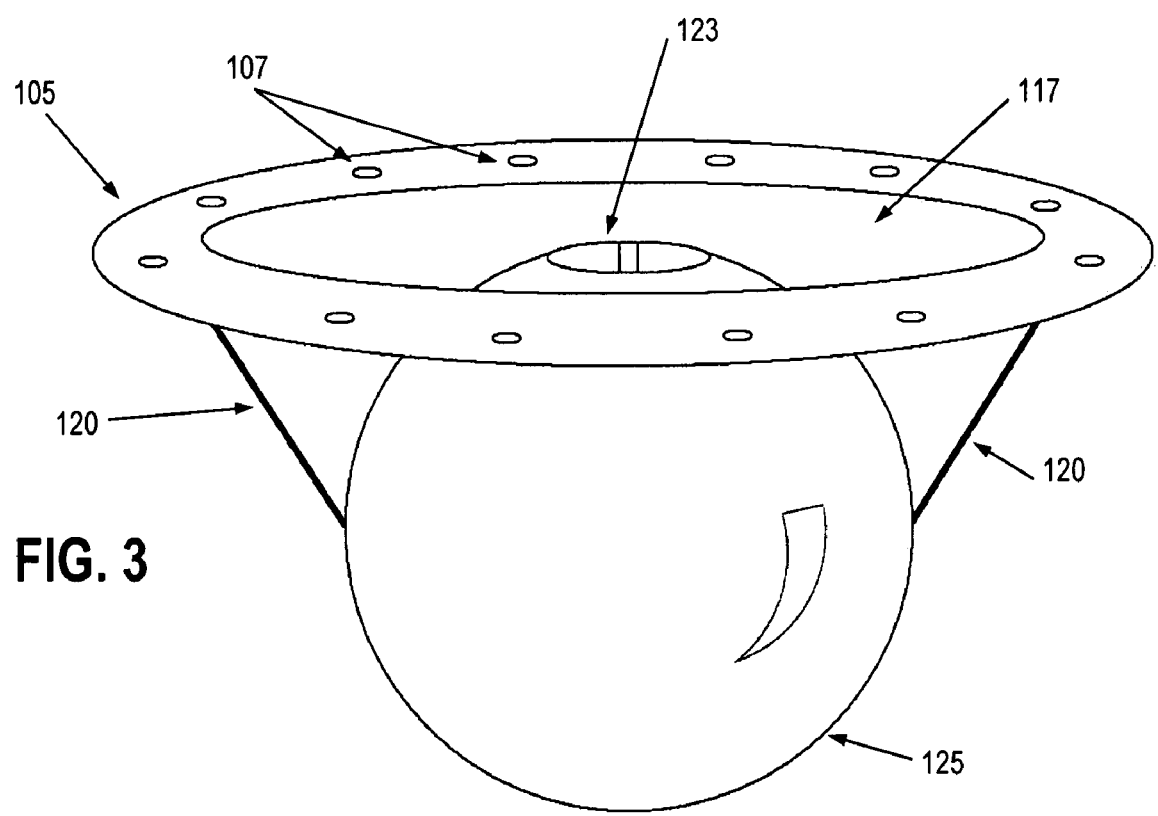
FIG. 3 illustrates an exemplary distal ring and impeding ball according to one embodiment of the disclosure.

FIG. 3 illustrates distal ring 105 having impeding ball 125 suspended partially within the plane of inner circumference 121 of distal ring 105. The location of impeding ball 125 creates an impedance or partial occlusion to the flow of solid and semi-solid material through central opening 117 of distal ring 105. The portion of central opening 117 that is open and allows material to pass through defines an effective orifice. Impeding ball 125 may swing or otherwise move from one side of inner circumference 121 to the other as the material passing through applies a force against it, thus affecting the size and/or configuration of the effective orifice and how fast material passes through (See FIGS. 5A-5C).

Figure 4:
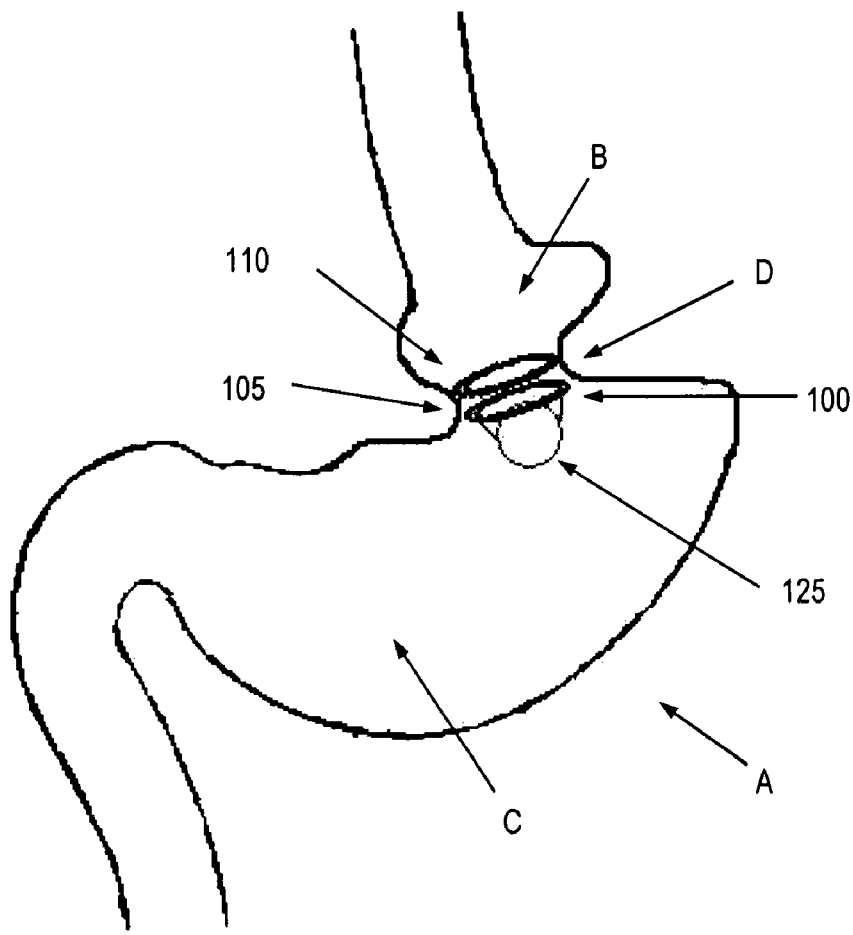
FIG. 4 illustrates the endolumenal implant implanted into a stomach according an exemplary embodiment.

FIG. 4 illustrates an exemplary application of implant 100 in a normal stomach A. Implant 100 may be securely positioned within stomach A at a predetermined location, thus creating a new opening or stoma D. Stoma D creates a subdivision in stomach A and thus forms a proximal chamber B and a distal chamber C. Implant 100 may be implanted in stomach A by various surgical procedures known in the art and may be disposed such that impeding ball 125 extends into distal chamber C.

Central opening 117 of distal ring 105 and proximal ring 110 may define the size of the created stoma D and a maximum possible effective orifice. Central opening 117 may be a relatively constant size, however, the size may also vary where distal ring 105 and proximal ring 110 are made of an elastic or resilient material. The positioning of impeding ball 125 with relative to distal ring 105 and proximal ring 110 will thus affect the configuration or size of the effective orifice. Ingested food material may apply a force upon suspended impeding ball 125 and may subsequently displace it laterally or vertically from its original location, discussed below.

Figure 5A:
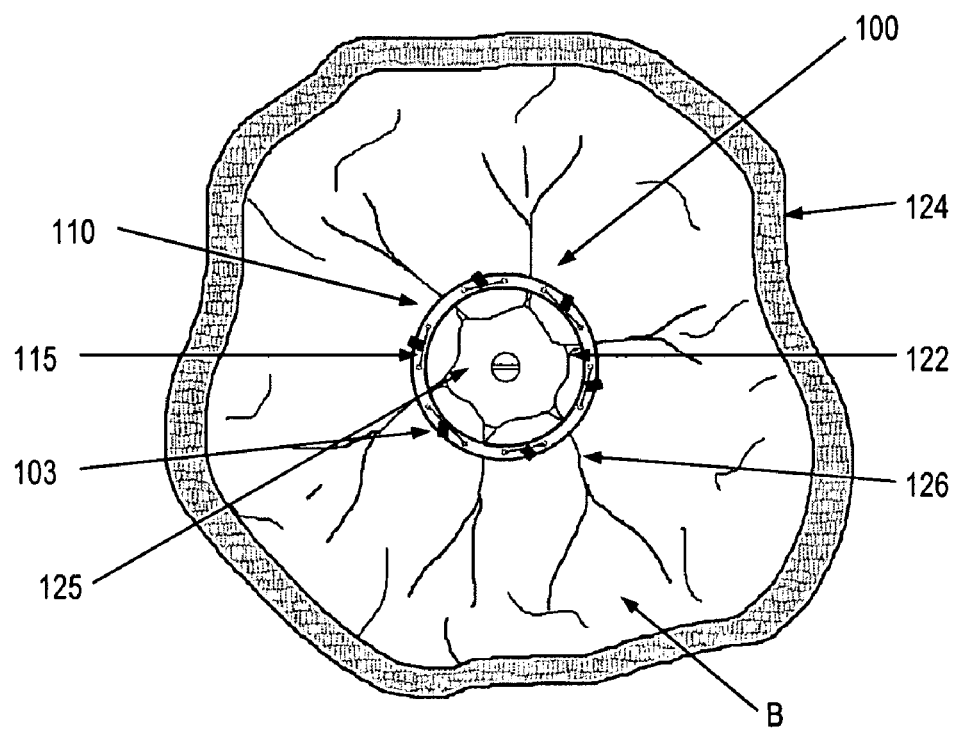
FIG. 5A illustrates a top view of an exemplary endolumenal implant implanted in a stomach according to the disclosure.

FIG. 5A illustrates a top down view of implant 100 as viewed from within the proximal chamber B. Pleats 122 of the gastric wall tissue 124 may be held or clamped between proximal 110 and distal 105 rings. In this illustration approximately six pleats 122 have been incorporated within distal rings 105 and proximal ring 110. The use of a dual-ring grasping engagement, with gastric wall tissue 124 disposed between the rings, provides a reliable and reinforced implantation of implant 100. The tension or pulling force that may be imposed on the grasped gastric wall tissue 124 may be radially distributed along the length of the surfaces of proximal ring 110 and distal ring 105 that engage tissue 124.

Between each of pleats 122 a plurality of spaces 126 may be created. Spaces 126 may serve as a vent for liquid and gas to pass from one stomach compartment to the other, eliminating a possible source of patient discomfort. Alternatively, a physician my choose to seal off spaces 126 by stripping or burning the mucosa of the tissue between the pleats, enabling the tissue to heal or fuse together. The physician may also utilize a suturing device to suture spaces 126 closed.

The implantation of distal 105 and proximal 110 rings, to form a stoma D of controlled size, creates an additional impedance for ingested food material. Stoma D and impeding ball 125 thus allow proximal chamber B to retain food material for a longer period of time than if there were no implant 100. It will be appreciated that the volume, viscosity, and/or digestive state of the food material may also be factors in determining how quickly material will pass through the stoma D. As the food material takes longer to pass through proximal chamber B it may be difficult or temporarily impossible for the patient to ingest more food material at one sitting. Further, this arrangement may additionally create a feeling of satiety, enabling the patient to voluntarily discontinue eating at the sitting.

Figure 5B:
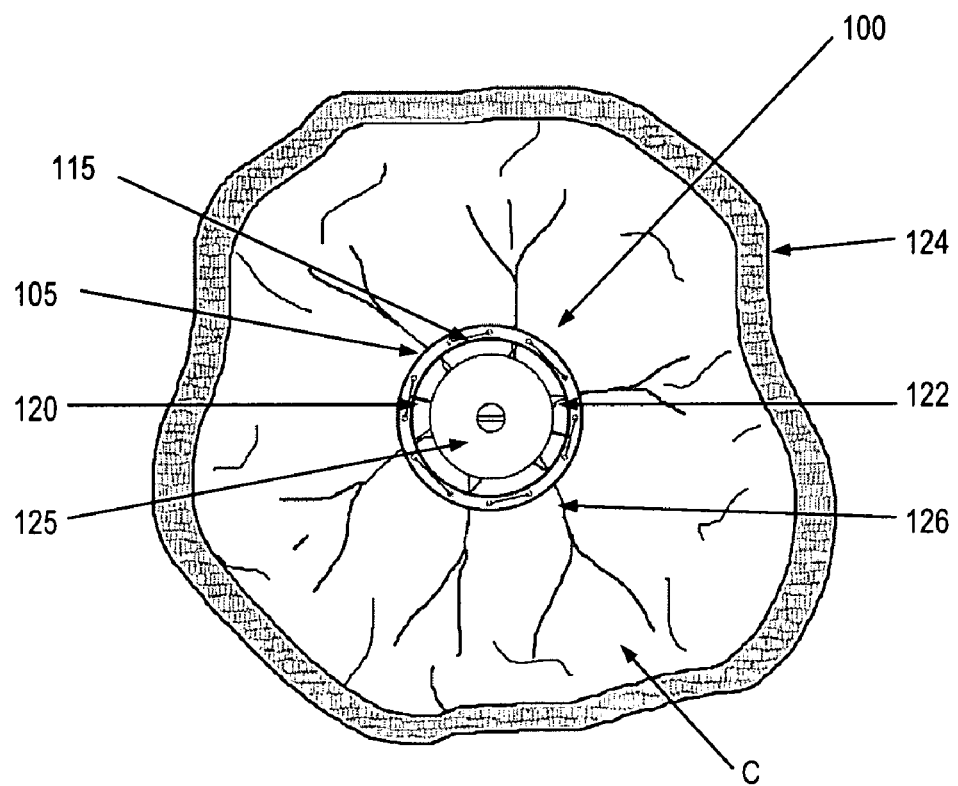
FIG. 5B illustrates a bottom view of an exemplary endolumenal implant implanted in a stomach according to the disclosure.

FIG. 5B illustrates implant 100 as viewed from within the distal chamber C. Impeding ball 125 is shown to hang into distal chamber C from suspension lines 120 at a predetermined length. After ingested food material passed through the created stoma D, it may travel naturally through the remainder of the digestive tract.

Impeding ball 125 may be made of a bio-compatible material that is resistant to the acids of the digestive system. The weight and density of the material of impeding ball 125 may chosen based on how easily impeding ball 125 may be moved aside or displaced by the force applied by the ingested food material within proximal stomach B. Stainless steel, titanium, plastic, gold, platinum, silicone, zirconium, nylon, ceramic, polypropylene, Teflon®, glass, silicone, etc. are all exemplary materials for construction of impeding ball 125.

Further impeding ball 125 may be adapted to be inflated. An inflatable impeding ball 125 may have an injection port (not shown) for introducing liquids therein. By injecting fluid into an inflatable impeding ball, the impeding ball would increase in volume, thereby decreasing the amount of the effective orifice area available for material to pass through distal ring 105. Conversely, by removing fluid from an inflatable impeding ball, the impeding ball would decrease in volume, thereby increasing the amount of effective orifice area available for material to pass through distal ring 105.

Impeding ball 125 may vary in size. The size of impeding ball 125 may also vary relative to the size of rings 105 and 110. Generally, impeding ball 125 has a diameter that is less than the diameter of the inner circumference 121 of distal ring 105. This prevents impeding ball 125 from becoming stuck within distal ring 105, preventing the creation of a possible one-way valve that may hamper the patient's ability to regurgitate material. The impeding ball 125 may be of a size that may be relatively easy to swallow and passed through the digestive track. For example, the size of impeding ball 125 may be in the range of 10-20 mm. It also enables gas to pass freely in either direction through the outlet D. As previously stated, impeding ball 125 may be made of or replaced with an object that has a shape that is other than spherical, such as an oval or football shape, cube shape, or irregular shape.

Suspension lines 120 may be made of a bio-compatible material that is resistant to the acids of the digestive system. One of skill in the art will appreciate that plastic, nylon, polypropylene, Teflon®, Gortex®, metal wire, cable, or any material that would be durable and have a long life in such an environment are all possible materials for construction of the suspension lines 121 and are within the scope of the disclosure.

Figure 6A:
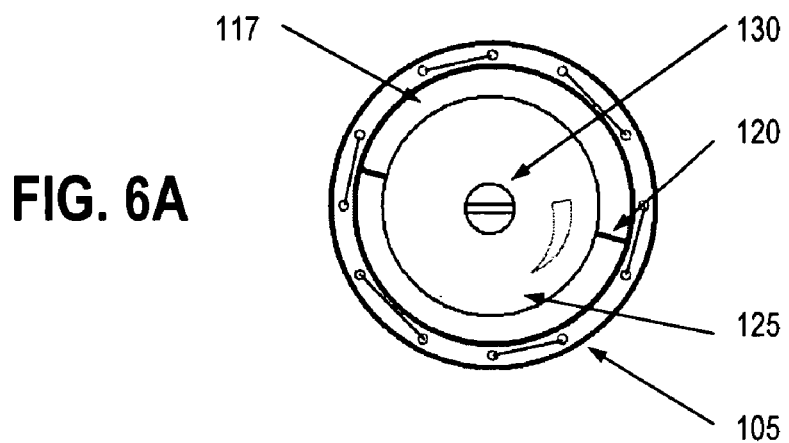
FIGS. 6A-6C illustrate the exemplary displacement of an impeding ball with respect to a distal ring.
Figure 6B:
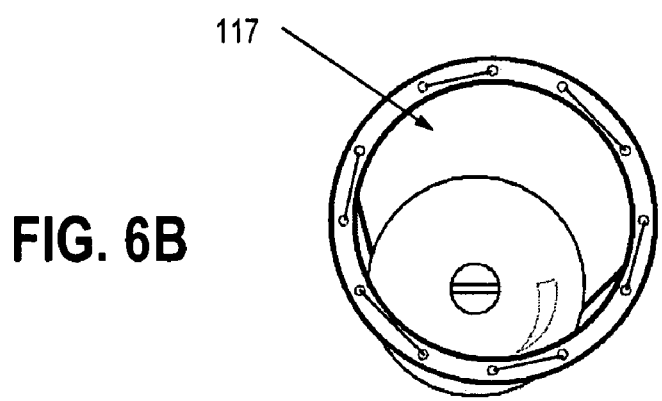
Figure 6C:
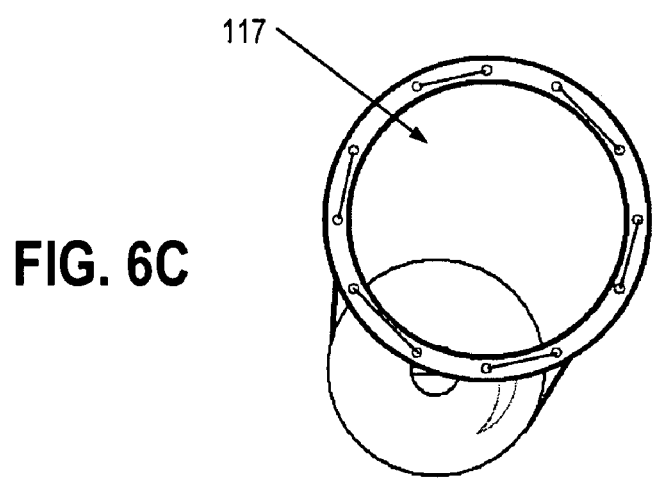

FIGS. 6A through 6C illustrate a configuration of the effective orifice of central opening 117 when impeding ball 125 is positioned in varied locations and with varying lengths of suspension lines 120. The configuration of the effective orifice illustrated in FIG. 6A has a generally circular or donut shaped opening. Whereas, the configuration of the effective orifice illustrated in FIGS. 6B and 6C has a crescent shaped opening. Ingested liquid may pass through the created stoma D (See FIG. 4) with impeding ball 125 in any location. The size, consistency, and/or viscosity of ingested food material (solid and semi-solid food pieces) within the proximal stomach chamber B will be a factor in determining the ease of which it may pass through the created outlet D. For example, depending upon the consistency of ingested food material it may pass more easily through a crescent shaped opening of FIGS. 6B and 6C, than that of FIG. 6A.

It has been shown in surgical bariatric procedures that weight-loss efficacy is effected by the size of the surgically created orifice. Generally, surgeons may attempt to create an orifice with an approximate diameter of 10 mm to 15 mm. This translates to an effective orifice area of 78 mm squared to 176 mm squared. One of skill in the art will appreciate that exemplary implant 100 may be configured to create a precise effective orifice area that is customized for a particular weight-loss regimen.

FIG. 7A illustrates a view of exemplary implant 100 with impeding ball 125 suspended at a predetermined distance from distal ring 105. FIG. 7B illustrates a view of exemplary implant 100 with impeding ball 125 suspended a further distance (relative to that shown in FIG. 7A) from the distal ring 105. As illustrated in FIGS. 7A and 7B, the size and/or configuration of the effective orifice area of central opening 117 may be determined by the displacement or location of impeding ball 125. More specifically, as the top 123 of impeding ball 125 approaches inner circumference 121 of distal ring 105, impeding ball 125 will begin to partially occlude a portion of central opening 117.

The length of suspension line 120 measured from the point of incorporation with distal ring 105 to the point of incorporation with impeding ball 125 may determine the displacement of top 123 of impeding ball 125, and consequently the size of the effective orifice of central opening 117. Accordingly, changing the distance between top 123 of impeding ball 125 and inner circumference 121 of distal ring 105 will change the amount or volume of material that can pass between the ball and the ring. As described above, the space defined between impeding ball 125 and distal ring 105 is referred to as the effective orifice area.

FIGS. 8A and 8B illustrate cross-sectional views of impeding ball 125 including a shaped hole 135 disposed substantially vertically therethrough, and a bore hole 133 oriented substantially perpendicular to shaped hole 135. An adjustment pin 130 may be rotatably located within shaped hole 135. Suspension lines 120 may attach at one end to distal ring 105, pass into bore hole 133, and may attach to adjustment pin 130 at the other end. Adjustment pin 130 may be capable of rotation in either a clockwise or a counter-clockwise direction. As adjustment pin 130 is rotated, suspension lines 120 may spool or un-spool around adjustment pin 130, thereby shortening or lengthening suspension lines 120, respectively.

A ratchet and tooth system (not shown) may be incorporated, which allows the pin to "click-in-place" in either direction with each fraction of a rotation. It will be appreciated that various one-way locking systems may be employed in order to provide a locking function as adjustment pin 130 rotates, such as a locking screw engagement, stepped locking tab, or a bracket system, and that such variations are within the scope of the disclosure.

Figure 9A:
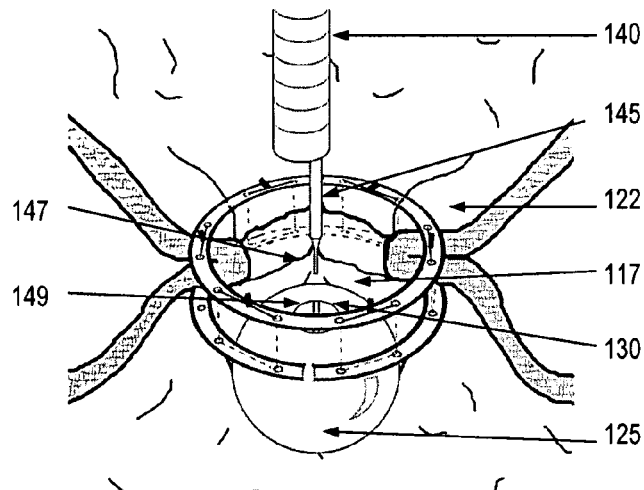
FIGS. 9A and 9B illustrate a perspective view of an exemplary device implanted within a stomach, and an endoscopic screw driver engaging the adjustment mechanism of the impeding ball.
Figure 9B:
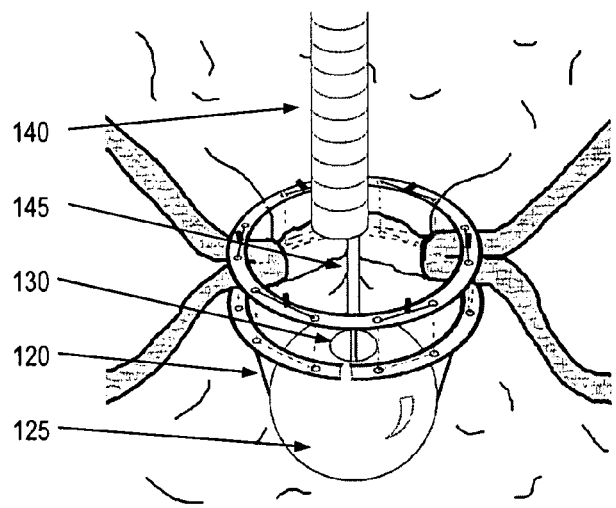
Figure 9C:
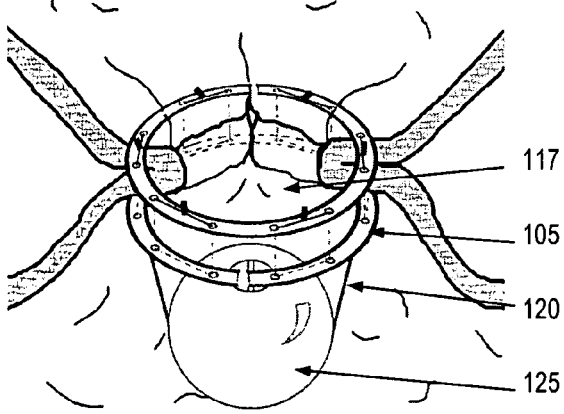
FIG. 9C illustrates an exemplary a perspective view of the implanted device within a stomach and having length adjusted suspension lines.

FIGS. 9A, 9B and 9C illustrate an exemplary endoscopic adjustment method for adjustment pin 130. FIGS. 9A and 9B illustrate the introduction of an endoscope 140 approaching the created stoma D and deploying an endoscopic tool 145 via an instrument channel in endoscope 140 Endoscopic tool 145 may be an adapted screw driver designed to engage adjustment pin 130 in impeding ball 125. Adjustment pin 130 may be turned (clockwise or counter clockwise depending on design) with an endoscopic screwdriver 145, which has a male distal tip 147 that may mate with the female groove 149 or concavity formed at either ends of adjustment pin 130. As adjustment pin 130 is turned, suspension lines 120 spool off or spool on adjustment pin 130, thereby increasing or decreasing, respectively, the length of suspension lines 120 exposed out of the bore 133. FIG. 9C illustrates a view of implant 100 where suspension lines 120 have been lengthened in relation to those shown in FIG. 9A.

The adjustability of the effective orifice of central opening 117 may be beneficial to the patient in that it allows a physician to selectively alter the patient's ability to intake food. This allows the physician to reduce the effective orifice of the stoma D if it is determined that the patient is not losing sufficient amounts of excess body weight. Alternatively, this allows the physician to increase the effective orifice of the stoma D if the patient is not receiving sufficient nutrition or is having other health or digestive related problems. For example, this may be a relevant issue with a patient having implant 100 in place and subsequently becoming pregnant, thereby requiring a higher degree of nutrition. In some cases it may be advantageous to remove impeding ball 125 completely, either permanently or temporarily.

FIGS. 10-12B illustrate another exemplary implant 200 according to the disclosure. Implant 200 utilizes suspension lines 220 coupled or positioned on opposing sides of distal ring 105. Suspension lines 220 have an attachment buttons 215 coupled to an end of suspension line 220 opposite the end which connects to distal ring 105. One of skill in the art will appreciate that attachment buttons 215 may be constructed of any material that will be attracted to a magnetic force, such as stainless steel and the like. Further, one having skill in the art will recognize that that attachment buttons 215 may be constructed of various sizes and shapes, as long as they have sufficient surface area to reliably magnetically engage magnetic points on the impeding ball.

FIG. 11A illustrates an impeding ball 240 having magnetic points 245 disposed substantially on the surface at opposing poles of impeding ball 240. FIG. 11B illustrates an impeding ball 250, similar to impeding ball 240, but having magnetic points 255 that are offset from the spherical poles. Magnetic points 255 may be incorporated into impeding ball 250 such that magnetic points 255 are a predetermined distance apart along the surface, but are not located opposite to one another. It will be appreciated by one having skill in the art that magnetic points 255 may vary in size and shape, and further may encompass a large portion or all of the surface area of impeding ball 250.

FIG. 11C illustrates a ball 260 of larger size in relation to impeding balls 240 and 250. It will be appreciated by one having skill in the art that impeding balls usable with implants 100 and 200 may be constructed in varying sizes in order to accommodate various design constraints, different orifice areas, and patient needs.

FIG. 12A illustrates impeding ball 240 including magnetic points 245 disposed on opposite poles thereof, which couples magnetically to attachment buttons 215. Accordingly, as magnetic points 245 mate with attachment buttons 215, impeding ball 240 may be suspended from suspension lines 220, below distal ring 105 and across central opening 117. Similarly, FIG. 12B illustrates impeding ball 550, having magnetic points 255 disposed at a different location than magnetic points 245 shown in FIG. 12A. Using impeding ball 255 instead of impeding ball 245, changes the distance from impeding ball 255 to distal ring 105, and this changes or adjusts the effective orifice.

Figure 13:
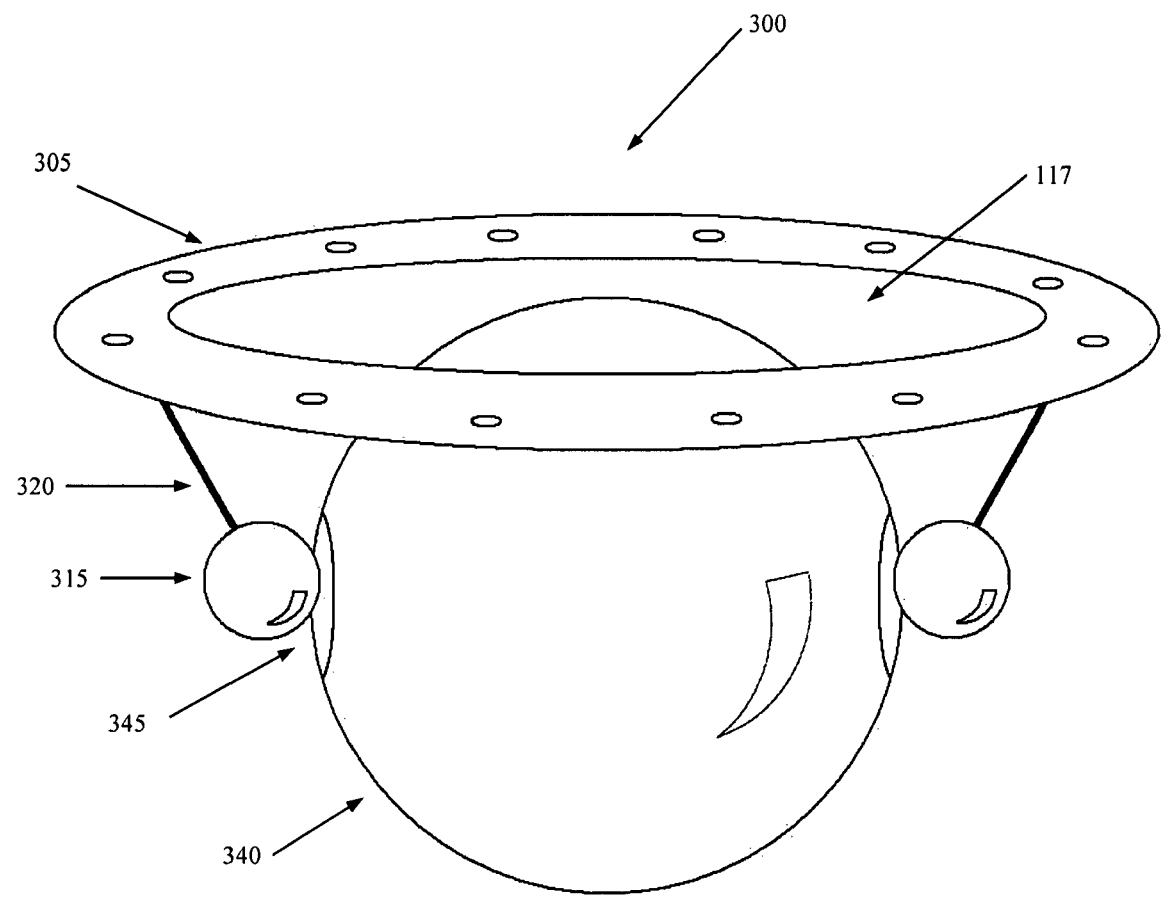
FIG. 13 illustrates a perspective view of a distal ring coupled to magnetic impeding ball according to yet another exemplary embodiment of the disclosure.

FIG. 13 illustrates another exemplary implant 300 having a magnetically releasable impeding ball 340. Similar to the above embodiment of implant 200 described above, a distal ring 305 is connected to suspension lines 320 having an attachment button 315, that magnetically couples with magnetic points 345 disposed on a surface of impeding ball 340.

Because the impeding ball (i.e. any of impeding balls 125, 240, 250, 260, and 340), may be held within the digestive system, it may act as a scaffold for continuous drug delivery. The impeding ball may contain, be made of, or be coated with a drug or drugs that may be released into the digestive system of the patient over a period of time. The impeding ball may deliver a variety of pharmaceuticals such as medicines for control of cholesterol, control of blood pressure, hormone therapy, birth control, acid control, appetite suppressants, anti-inflammatory, anti-depressants, etc. The medication delivered by the impeding ball may be designed to last a predetermined period of time. Further, periodic removal of the depleted impeding ball and replacement with a new impeding ball may be scheduled to coincide with periodic endoscopic check-ups.

It is also noted that distal and proximal ring material and may also be made of, contain, or be coated with a biodegradable substance, such as a medication, that may deliver a steady dose of medicine over time. This substance could be, for example, an appetite suppressant, a proton pump inhibitor, an anti-inflammatory drug, or other medication. The medication may be an appetite suppressant that is delivered for a determined amount of time to assist a patient in assimilating to their new eating pattern after implantation of the implant.

Furthermore, the impeding ball, being held within the digestive system may act as a scaffold for housing a variety of electronic devices. For example, the impeding ball could contain a imaging device (e.g. a camera) or a device that has the ability to measure conditions within the stomach such as a PH level sensor and/or a temperature sensor and can then transmit that information to a receiver outside the patient's body. Further, the impeding ball may contain a computer chip that can store information such that the information can be retrieved with a reader outside the patient's body. The chip could store a patient's history of personal medical data. The impeding ball may also act as a pacemaker-like device to deliver low-level electrical stimulation to the stomach. This pacemaker-like device or gastric stimulator may serve to aid in the treatment of obesity.

Figure 14:
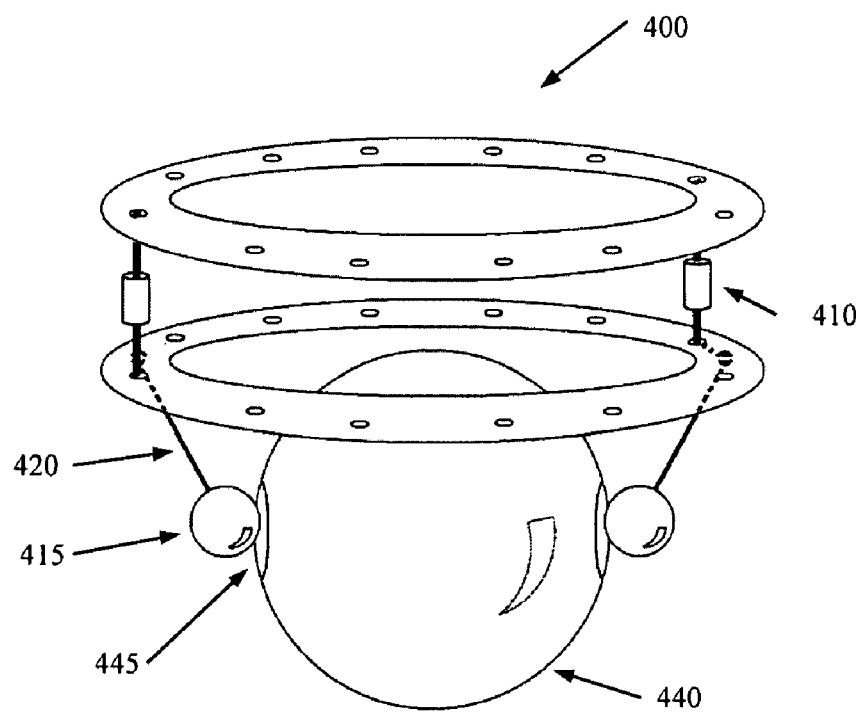
FIG. 14 illustrates a perspective view the device of FIG. 13 having a proximal ring and an electronic lead connector according another exemplary embodiment.
Figure 15:
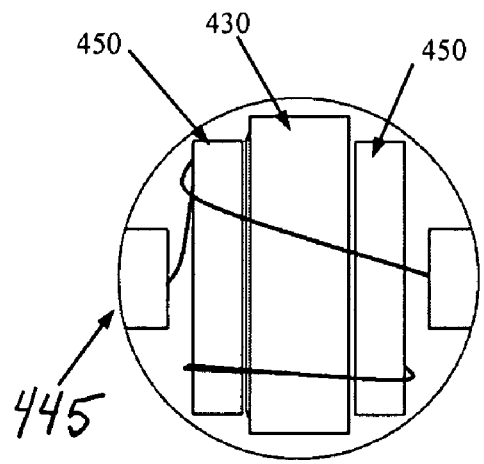
FIG. 15 illustrates a cross-sectional view of yet another exemplary embodiment, where the impeding ball includes an electronic device.

FIGS. 14 and 15 illustrate an exemplary implant 400 that includes an impeding ball 440 having an electrical device disposed therein that may deliver electrical pulses to the patient's body similar to the functioning of a pacemaker. In this case, impeding ball 440 includes magnetic points 445, conductive buttons 415, conductive suspension lines 420, and leads 410 (FIG. 14), which may be electrically connected to circuitry 450 and a battery 430. The structure shown in FIG. 15 may be disposed within impeding ball 440. Battery 430 supplies electrical energy for sending low-level electrical pulses to the surrounding gastric tissue 124 (See FIGS. 5A & 5B) thus creating a gastric stimulation device. Circuitry 450 may transform the energy from the battery 430 into low-level electrical pulses. Circuitry 450 also may control the timing of the electrical energy and the amount of energy delivered.

Leads 410 may be electrically connected to impeding ball 440, and circuitry 450, and battery 430 contained therein. Leads 410 may be connected to or formed with conductive suspension line 420. Suspension line 420 may be made from a conductive material (to allow an electrical signal or pulse to pass through) known in the art and further may be coated in a non-conductive material, such that electrical pulses are delivered only at leads 410. Conductive attachment buttons 415 connect magnetically and electrically to magnetic points 445. In the event that the location of electrical stimulation is desired at a location proximal or distal to implant 400, a length of lead 410 running from conductive suspension lines 420 may be attached (not shown).

It is believed that through low-level electrical pulses, therapy provided by pacemakers and gastric stimulators may slow the intrinsic electrical waves in the stomach. This electrical stimulation may cause the stomach to relax, resulting in distension of the stomach. This distension may trigger nerves in the stomach involved in digestion to send signals via the central nervous system to the brain that the stomach is "full."

Implant 400 may be programmed to transmit the signals on a designed or personalized schedule, thereby reducing feelings of hunger at times previously associated with eating/overeating, for example at dinner time or evenings. In another embodiment (not shown), the impeding ball has the ability to receive signals from outside transmitters to activate the electrical pulses. This may allow placement of transmitters near refrigerators, pantries and cupboards, or any area of food storage or disbursement, thereby reducing the temptation to eat.

Traditional pacemakers and gastric stimulators require a surgical procedure to access the device and replace it once the batteries have been depleted. In the embodiment of the present invention, implant 400 containing a gastric stimulator or electronic device may be replaced by simply retrieving impeding ball 440 from the patient using endoscopic instrumentation through the patient's mouth and replacing an impeding ball with fully charged batteries.

In the event that a physician determines that an impeding ball needs to be replaced, he or she may simply replace the existing impeding ball with another impeding ball. It may be decided that the effective orifice of distal ring 105 needs to be altered, in such a case an impeding ball with an alternate magnet configuration (as shown in FIGS. 11A and 11B) may be used. As illustrated in FIG. 12B, when impeding ball 250 (having magnetic points 255 in alternate locations) is employed, impeding ball 250 will be suspended below the height of and impeding ball 240, as shown in FIG. 12A. Additionally, an impeding ball having a larger or smaller size, e.g. the larger sized impeding ball 260, may be employed to achieve a modified effective orifice.

Further, the physician may decide to replace the impeding ball for a variety of reasons. For example, it may be that the batteries in an electronic device within the impeding ball may have expired, or medication to be delivered has been depleted. In both of these cases a new impeding ball may be employed with revived batteries or supply of medicine.

The procedure of exchanging impeding balls may be performed endoscopically by simply grasping the impeding ball with an endoscopic net, or other foreign body endoscopic grasper, and then extracting the impeding ball. For example, the impeding ball may have a channel running through it (not shown) to enable the passage of a guide-wire (not shown) through the ball. With the guide-wire traversing the impeding ball, an endoscope may simply push the ball down to position, incorporating the impeding ball with distal ring 105 as the magnetic points of the impeding ball attract and align to attachment button 215 of suspension lines 220.

The impeding ball may also be temporarily connected to the end of a suction hose and held in place via the vacuum of the suction hose (not shown). The hose, with the releasably attached impeding ball may be advanced endoscopically down into the position, such that magnetic points may align with attachment buttons 215. The impeding ball may then be released from the suction hose by deactivating the vacuum.

Similarly, the impeding ball may be grasped and removed from its position inside stomach A via attachment to the suction hose. The suction hose may be positioned endoscopically (not shown) with its distal opening adjacent to the impeding ball, and once the vacuum is activated, the ball will be releasably coupled to the suction hose. It is noted that the vacuum pressure needs to be of adequate strength so to create a vacuum force with the impeding ball that is greater than the magnetic force between the magnetic points of the impeding ball and attachment buttons 215.

A replacement impeding ball may again be endoscopically lowered, or simply swallowed into place and the attachment buttons 215 of suspension lines 220 would magnetically align to the magnetic points of the new impeding ball. If a physician determines that a patient would be better served, either temporarily or permanently, without an impeder ball, then the physician may choose to not replace the impeding ball once removed. The proximal and distal rings may remain in place in the patient even when the impeding ball is removed. This provides the patient the option to replace the impeding ball months or years from an initial removal, if it is determined that weight control is again needed. Further is it noted that if by some chance an impeding ball becomes accidentally detached from its suspension lines, it may simply be passed through the digestive system and be excreted naturally.

The magnetic attachment of the suspended impeding component allows for the simple attachment, detachment, and re-attachment of the suspended impeding components. In the above embodiment, endoscopic foreign body retrieval and delivery instrumentation are examples of tools needed to perform an adjustment of the effective orifice area of the created stoma D, however, one having skill in the art will appreciate that various endoscopic methods may be employed in order to add or remove a magnetically attached impeding ball.

FIGS. 16A-16D illustrate the movement of impeding ball 340 and the flexibility of distal ring 305. It is noted that a proximal ring (not shown) would respond to external forces similar to the distal ring 305. The distal ring 305 and proximal ring may typically be made out of a flexible material. Flexible material helps facilitate endolumenal implantation of the ring and allows the created stoma D to flex or change in shape to accommodate the movement of the stomach and the food material moving through therethrough. This flexibility also helps to decrease the possibility of tissue tearing away from either or both of the distal and/or proximal rings, something that could happen more easily if the rings were rigid. As discussed above, the rings may or may not have elastic qualities. One of skill in the art will appreciate that distal and proximal rings may be made from a variety of biocompatible materials, flexible or inflexible, such as metal, plastic, rubber, silicone, Buna-N, Neoprene®, Teflon®, Dacron®, fabric, or a composite materials, as is within the scope of the invention.

Figure 16A:
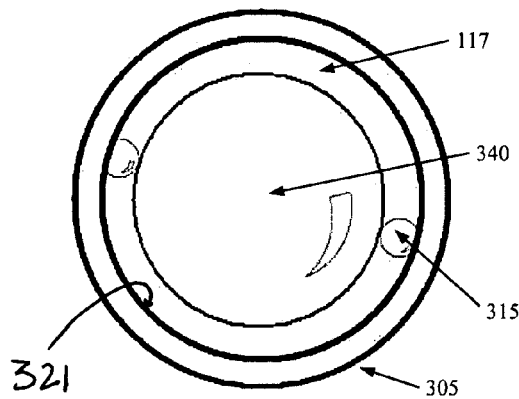
FIGS. 16A-16D illustrate an exemplary flexible ring and an exemplary displacement of an exemplary impeding ball with respect to the flexible ring.
Figure 16B:
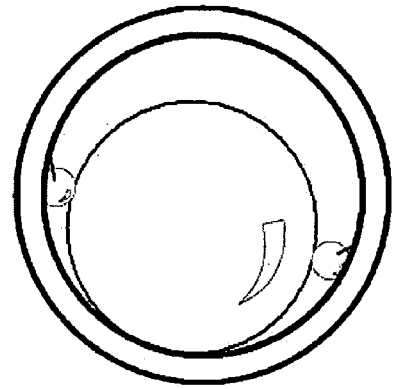
Figure 16C:
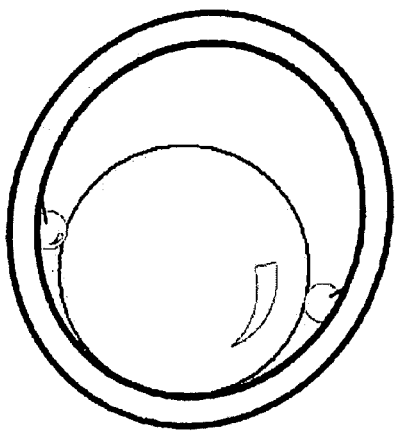
Figure 16D:
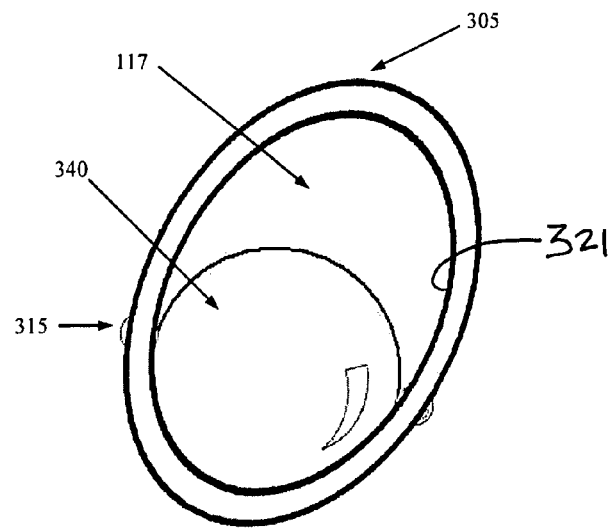

With further regard to FIGS. 16A-16D, it can be seen that the impeding ball 340 may be repositioned (e.g., free-swinging) relative to the position of distal ring 305. Moreover, it can be seen that the shape of the distal ring 305 may change where the distal ring is made from a flexible material as discussed above. As such, the effective orifice area may remain constant in size, but fluctuate in shape. For example, when the impeding ball 340 is positioned substantially concentric with the central opening 117, as shown in FIG. 16A, the effective orifice area is "donut-shaped," wherein a narrow opening circumscribes impeding ball 340. When the impeding ball 340 is positioned such that it comes in contact with the inner circumference 321 of distal ring 305, as shown for example in FIGS. 16B-16D, the effective orifice area is "crescent-shaped," wherein a wider opening between the impeding ball 340 and the inner circumference 321 of the distal ring 305 has been created. This enables a masticated food bolus of a relative size and viscosity to be delayed proximal to the impeding ball 340 until either the shape of the effective orifice area to accommodate the bolus, and or the bolus is further digested enabling it to pass through the orifice area.

FIGS. 17A-23 illustrate an exemplary means for attaching or implanting the implant, according to the disclosure, into a stomach. Suturing devices described in U.S. Pat. No. 6,464,707 to Bjerken, U.S. patent application Ser. Nos. 11/327,348, 11/267,266 both to Bjerken, and U.S. Provisional Pat. Application No. 60/791,214 to Bjerken, are hereby incorporated by reference in their entirety for all purpose as if fully set forth herein. The aforementioned devices and methods may enable an operator to remotely place suture material within a closed space such a hollow body organ. Such devices enable the endolumenal implantation of prostheses, correction of defects, and the reconfiguration of tissue without the need for surgical incisions.

The suturing devices described in U.S. patent application Ser. No. 11/327,348 and U.S. Provisional Pat Application No.

60/791,214 specifically describe the implantation of a set of circular grafts anchored to one another containing and effectively holding gastric tissue between them. The circumferential gathering and connection of tissue within the stomach creates a proximal stomach chamber with a limited volume and a narrowed outlet or passageway leading to the remainder of the digestive system.

Figure 17A:
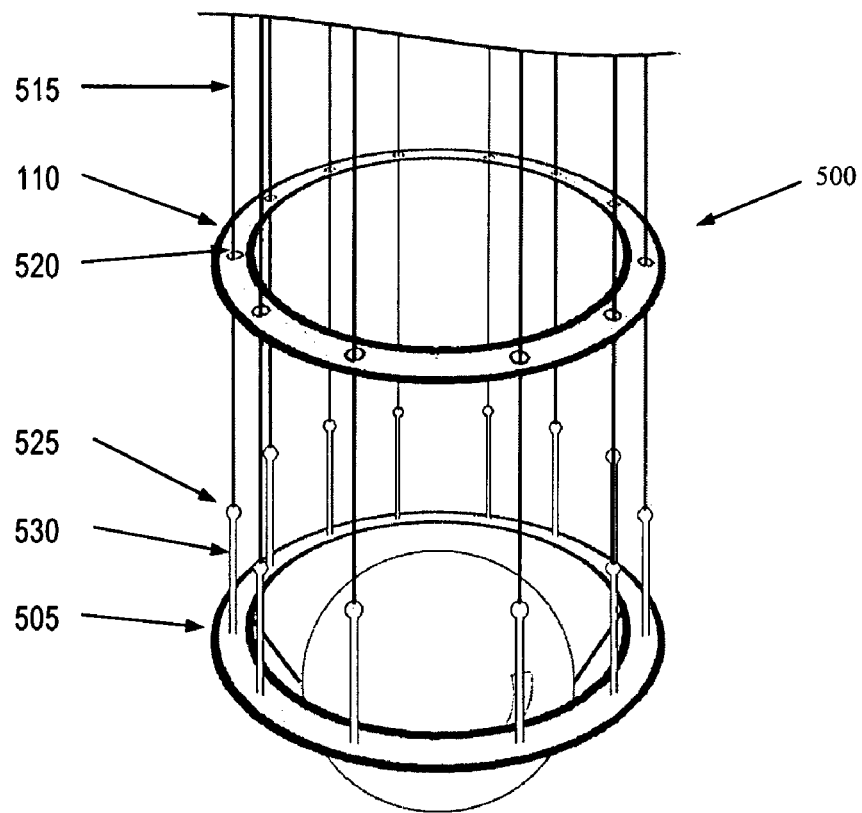
FIG. 17A illustrates a perspective view of another exemplary embodiment, where the proximal and distal rings are coupled together along suture lines and pins.
Figure 17B:
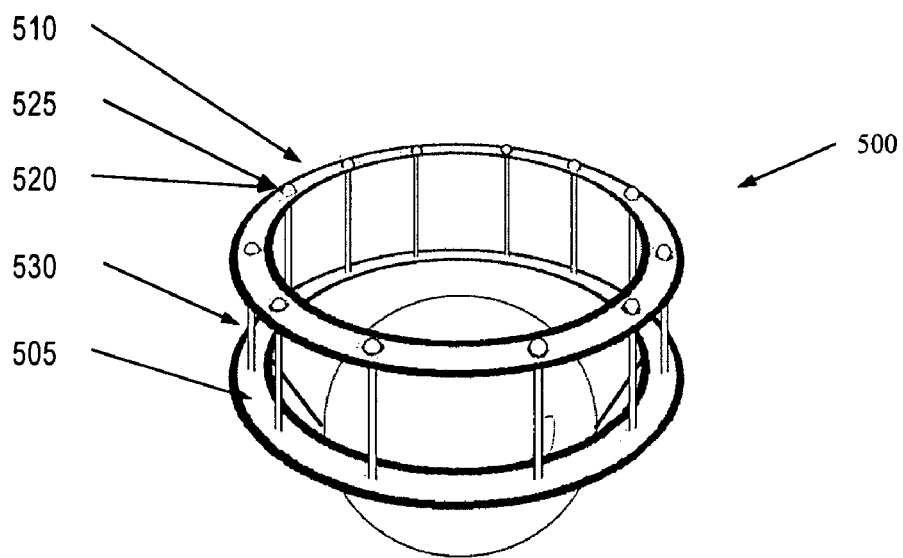
FIG. 17B illustrates a perspective view of the embodiment of FIG. 17A wherein the proximal and distal rings fit together with a snapping relationship.

FIGS. 17A and 17B illustrate an exemplary implant 500 having a unique endolumenal attachment means. Proximal ring 110 and distal ring 505 may be formed such that they can fasten together to eliminate the need to tie or otherwise secure sutures 515. Needles 509 and sutures 515 (See FIG. 19) are coupled with male connection members 530. One of skill in the art will appreciate that the coupling arrangement between sutures 515 and male connection members 530 may include integral forming, use of adhesive, or sutures 515 may be run through the male connection members 330 (not shown). As illustrated in FIGS. 17A and 17B, male connection members 330 of the distal ring 505 have distal anchors 525. Distal anchors 525 are of a size small enough to be pulled through a female connection opening 520 of proximal ring 110, yet large enough so resist return of distal anchors 525 through the female connection opening 520.

In use, distal ring 505 is incorporated with the tissue using an endolumenal suturing device (described below). Proximal ring 110 may slide down along sutures 515 and may be positioned above the incorporated tissue (not shown) and distal ring 505. Tension on sutures 515 may provide upward force on distal ring 505, while endoscopic instrumentation, such as a graft pusher, applies downward force on proximal ring 110. The male connection members 530 of distal ring 505 may then extend through the incorporated tissue. The upward force (created by tension on sutures 515) on distal ring 505 may be combined with the downward force on proximal ring 110, thus enabling male connection members 530 to apply a force on proximal ring 510. Then distal anchors 525 are pushed through the female connection openings 520 enabling a "snap" connection and thereby fastening distal ring 505 to proximal ring 110 (See FIG. 17B) with the tissue folds (not shown) fixated therebetween. Sutures 515 may then be cut using endoscopic instrumentation known in the art.

FIG. 18 illustrates an exemplary double-armed suture 550 used in exemplary suturing devices 600 and 700, described below. Double-armed suture 550 may be described as two needles 509 attached to one another by a length of suture material 515 at non-sharpened endpoints 555. Needles 509 are made of a material that has the property of shape memory, such a material may be Nitinol wire. One having skill in the art will appreciate that various materials may be used to manufacture needles 509 such that it may react and retain a given shape and that such variations are within the scope of the disclosure.

Needles 509 may be of a length sufficient to be able to extend at least twice the length of suturing devices 600 and 700, described below. Therefore, if suturing devices 600, 700 are, for example, 2.5 feet, then needle 509 may be at least 5 feet in length. Needles 509 are attached to connecting suture material 515, which may be at least as long as the combined length of two attached needles 509.

Figure 20A:
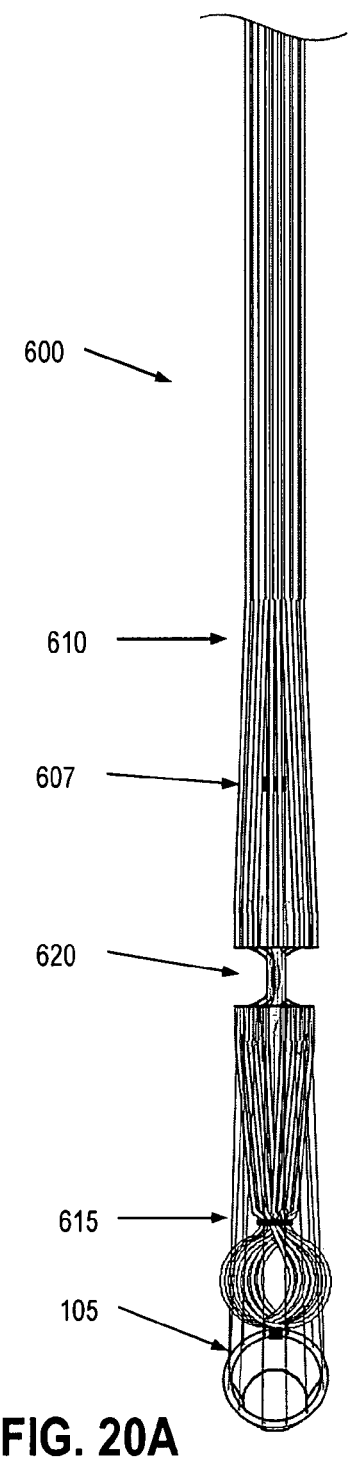
FIG. 20A illustrates an exemplary suturing device with an unexpanded suture engagement area.
Figure 20B:
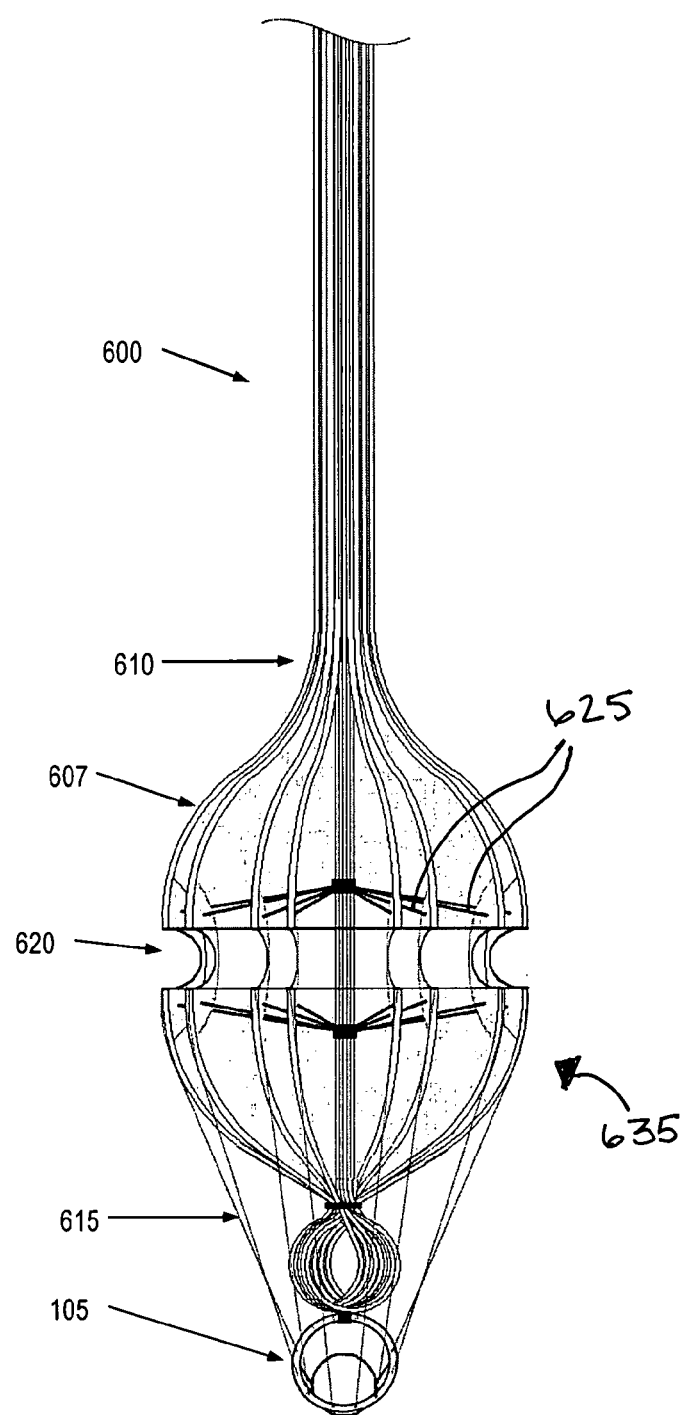
FIG. 20B illustrates an exemplary suturing device with an expanded suture engagement area.

One having skill in the art will recognize that suture material for use in exemplary suturing devices 600, and 700 may be made of any commonly used surgical suture material, such as braided, non-braided, or composite structures, as long as they work well for traveling through cannulas 507 and 607 (See FIGS. 19, 20A and 20B). For example, a double-armed suture, as illustrated in FIG. 18, may have a length made of a braided monofilament polypropylene suture material attached in the middle, enabling exemplary distal ring 505 of exemplary implant 500 to be looped with the monofilament polypropylene suture material and therefore be implanted and fixed within an organ.

FIG. 19 illustrates how double-armed sutures 515 and needles 509 are backed into flexible cannulas 507 within exemplary suturing devices 600 and 700. The length of suture 515 connecting the two needles 509 may be looped through distal ring 505 of implant 500. Further, the distal ring 505 may be previously incorporated with the suture 515 at distal anchors 525, by various attachment means known in the art.

Figure 21:
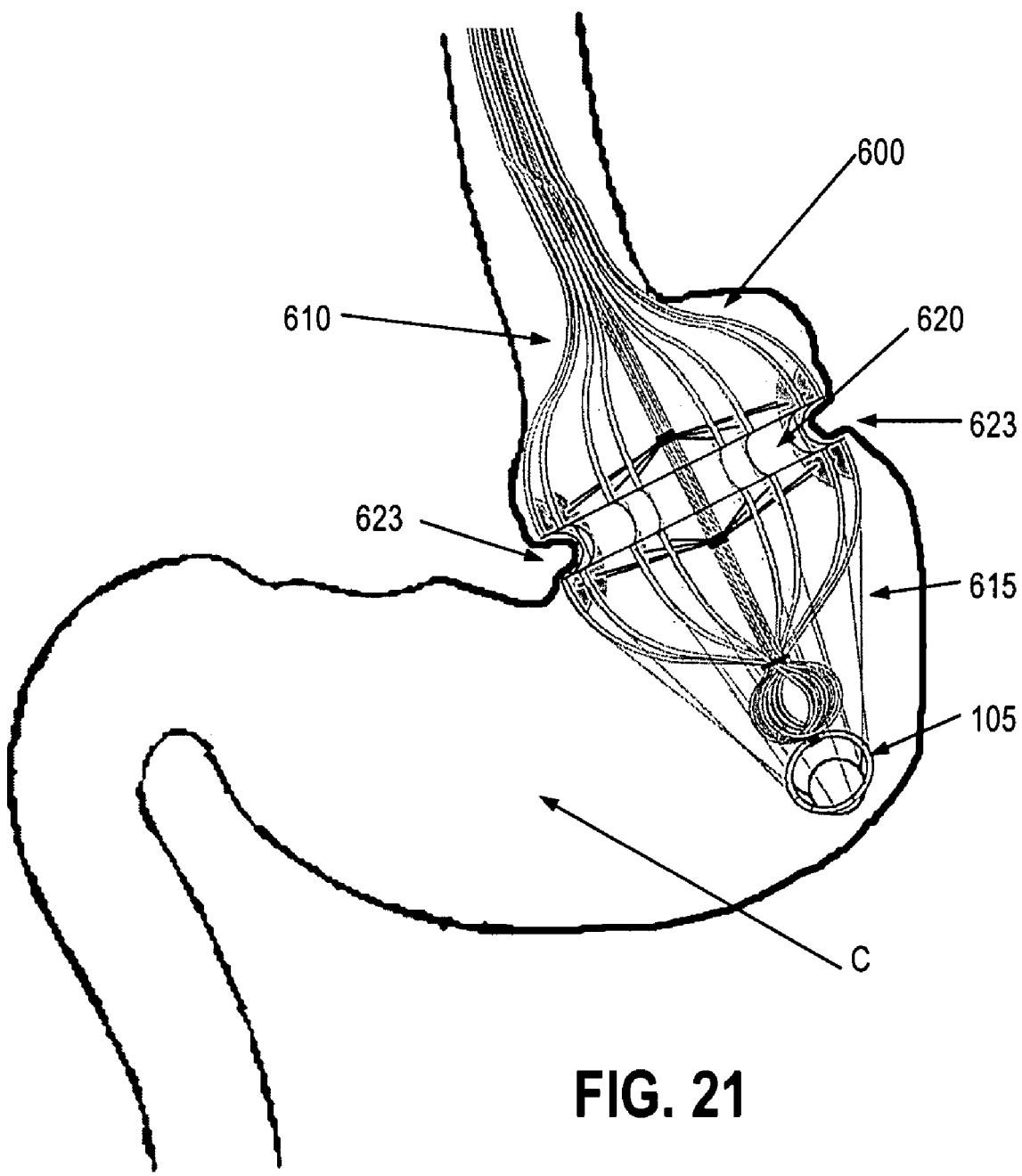
FIG. 21 illustrates a cutaway view of the exemplary suturing device of FIGS. 18A and 18B disposed endoscopically inside a stomach.

FIGS. 20A, 20B, and 21 illustrate an exemplary implantation device 600 in collapsed and expanded states. Similar to above, distal ring 105 may be previously incorporated with suture material 615 by various attachment means known in the art. To implant the proximal and distal rings described above into a stomach, suturing device 600 may be pre-loaded with the distal ring 105 and then inserted endoscopically in its collapsed configuration, as shown in FIG. 20A, through the patient's mouth. Once inserted into the stomach, in this embodiment, an expandable portion 635 of the suturing device 600 may be expanded (FIG. 20B) via expanding rods 625 to increase the diameter of the suture engagement area or drawn-in tissue area 623 (FIG. 21). A suction channel 620 is formed to at least partially circumscribe expandable portion 635. It will be appreciated by one having skill in the art that suturing device 600 may be expanded by various methods, such as negative vacuum pressure or another expanding rod configuration, as long as it may be controlled endoscopically, and that such are with in the scope of the disclosure.

FIGS. 22A and 22B illustrate a further exemplary aspect of the implantation process. Suturing device 600 may then be pulled in a direction towards the patient's head such that the expanded portion 635 may be situated in the top of the stomach. A vacuum force may be applied, drawing stomach tissue (FIG. 21) into suction channel 620. In this embodiment, cannulas 607 are back-loaded with suture material 615 and needles 609.

As illustrated in FIG. 22A, the long needles 309 that are back-loaded into and extend out of a proximal end of delivery cannulas 607A and a main tube 640. Consequently this arrangement enables the operator to manually or mechanically manipulate needles 609 in delivery cannulas 607A. During implantation needles 609 cross the suction channel 620 (See FIG. 21), penetrate drawn-in tissue 623, and extend back up into receiving cannulas 607B.

As illustrated in FIG. 22B, the needles are grasped and pulled completely through and out of receiving cannulas 607B of suturing device 600, leaving a portion of suture material 516 extending through drawn-in stomach tissue 623. The vacuum may be deactivated and expandable area 635 of suturing device 600 may then be collapsed. Distal ring 105 may be releasably held in place on the suturing device 600 by sutures 615, and is released as suturing device 600 is withdrawn from the patient. Suture material 615 may then be incorporated and anchored in the stomach wall tissue, such that it stays in place at drawn-in tissue portions 623 as the suture material 615 is pulled out of receiving cannulas 607B as suturing device 600 is withdrawn. Tension of sutures 615 may be manipulated to position distal ring 105.

In this embodiment, gastric ring 105 is pre-loaded on suturing device 600, as described above. A suture/needle organizer may be employed to maintain the order of the needles as they are situated about a circumference of tube 640. If a proximal ring is to be utilized, needles 609 may pass through and be incorporated into the proximal ring. The operator may use an endoscope or other graft pusher to push and slide the proximal ring down the patient's esophagus and into the stomach as proper tension is maintained on sutures 615, such that the proximal ring slides down the sutures (not shown). The proximal ring may then be lowered into a predetermined position with incorporated tissue folds, e.g. drawn-in tissue 623, separating the proximal ring from distal ring 105. The sutures 615 may then be secured by a variety of methods. For example the operator may use suture anchors 103 (See FIG. 1), tie suture material 615, or use a self-fastening mechanism illustrated in FIGS. 17A and 17B.

Once suture material 615 is secured to proximal and distal rings and pulled through such that a portion exits suture device 600, the exposed suture material may be cut and withdrawn from the patient. The implant is thus implanted in a stomach A or other endolumenal passage, as illustrated in FIG. 4, creating a small proximal chamber B at the top of the stomach with a narrow outlet or stoma D leading into distal stomach C.

Figure 23:
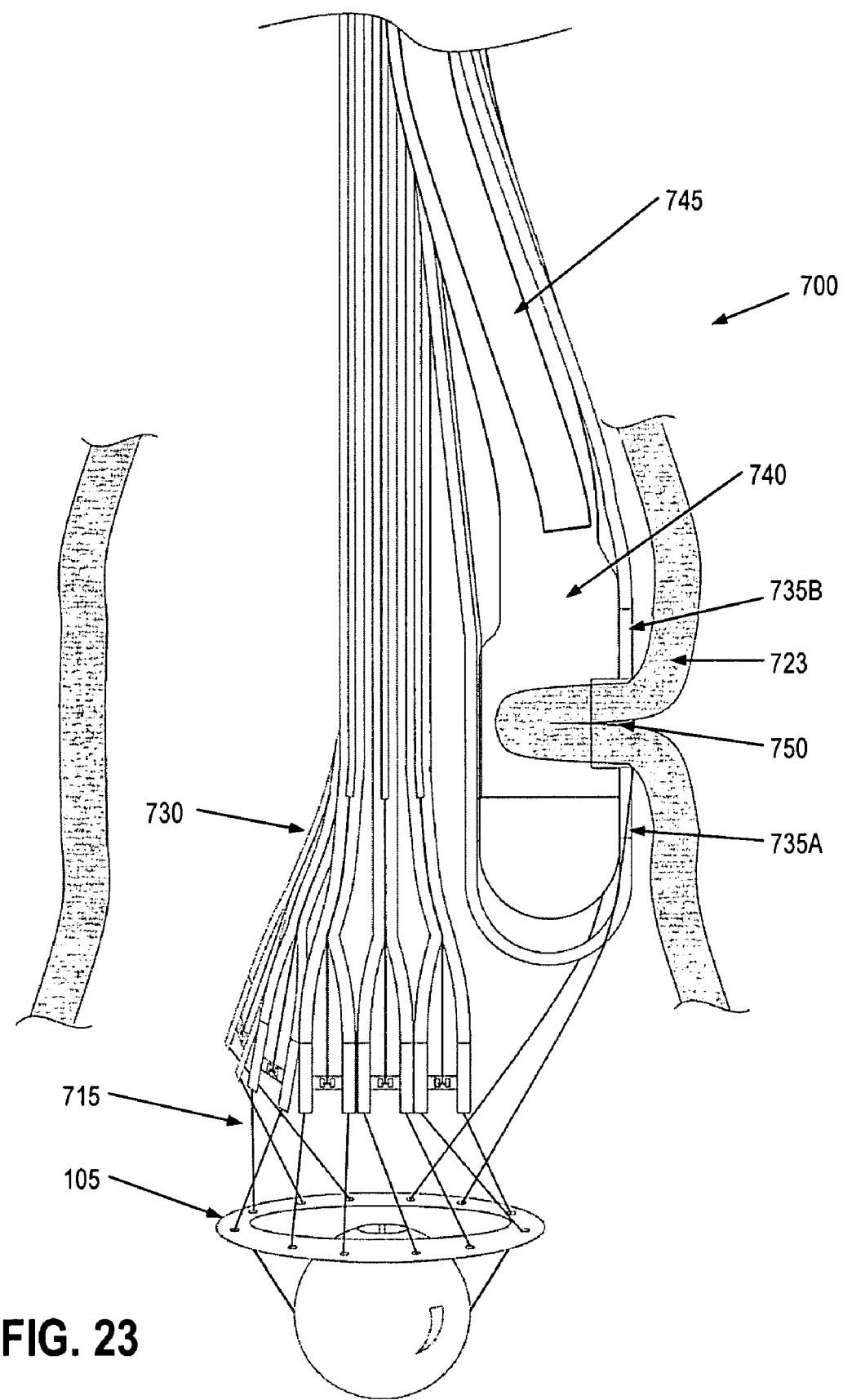
FIG. 23 illustrates another exemplary embodiment of an exemplary suturing device.

FIG. 23 illustrates another exemplary suturing device 700 that may be utilized to install the implant according to the disclosure. Similar to that which is described above, distal ring 105 may be previously incorporated with the double-armed sutures 715 by various attachment means known in the art, such as passing double-armed sutures 715 through at least two apertures in distal ring 105. A series of delivery cannula sets 730 loaded with double-armed sutures 715 (as shown in FIG. 18) are positioned within a hollow organ or body cavity, e.g. a stomach. A distal ring 105 may be coupled to suturing device 700 via double-armed suture material 715. In this embodiment, each double-armed suture 715 may be delivered and incorporated with drawn-in tissue 723 individually, that is one set at a time.

FIG. 23 illustrates the exemplary functioning of suturing device 700. A suction capsule component 740 and an attached tube 745 may be in fluid communication with a vacuum source (not shown). When the vacuum source is activated, negative pressure will draw-in tissue 723 adjacent to a suction opening 750 of suction capsule component 740, wherein the drawn-in tissue 723 is a fold of tissue. At this point at least one delivery cannula set 730 may be warped to mimic a perimeter of a suction capsule 740. As delivery cannula set 730 wraps about suction capsule component 740 a distal cannula end 735A may be disposed at a lower side of drawn-in tissue 723, and a proximal cannula end 735B may be disposed at an upper side of drawn-in tissue 723. When distal cannula end 735A of the delivery cannula set 730 is warped, suture material 715 may by formed between distal cannula end 735A and distal ring 105.

Drawn-in tissue 723 may now be ready to receive the needle (not shown) and double-armed suture material 715 that may be advanced through warped delivery cannula set 730. The needles (See FIGS. 18 and 19) with attached double-armed suture material 715 may now enter and be fed through warped delivery cannula set 730, such that the needle passes from distal cannula end 735A, penetrating and traversing drawn-in tissue 723, and back into proximal cannula end 735B, wherein traversing at least includes passing through the drawing-in tissue 732 or fold. Traversing It will be appreciated by one of skill in the art that a reverse direction of the feeding of the needle may be utilized and is within the scope of the disclosure. Once an end of the needle emerges out of an end of delivering cannula set 730 that is external to the patient's body, the needles may be grasped and pulled completely out of the delivering cannula set 730, thus drawing attached double-armed suture material 715 through the tissue.

After passing a the need and double-armed suture material 715 through drawn-in tissue 723, the delivery cannula set 730 that was warped about suction capsule component 740 may be disengaged therefrom, leaving used cannula set 730 in place on drawn-in tissue 723. Leaving the receiving cannula set 730 in place may serve to maintain the implanted double-armed suture material 715 in order within the lumens (not shown) of receiving cannula set 730.

In order to prevent strands of flaccid double-armed suture material 715 running up a patient's esophagus, or other tubular organ, the strands are held within the more easily manageable delivery cannulas sets 730. This may be necessary in order to maintain double-armed suture material 715 and the associated needles in proper order. The delivery cannula set 730 that had just delivered the back-loaded double-armed suture material 715 is now empty and may be disengaged from the suction capsule component 32 and removed from the suturing site, or it may be utilized as a subsequent receiving cannula set 730. The suction capsule component 740 is now available to be coupled with a subsequent delivery cannula set 730. This is repeated until all intended sutures have been incorporated with the endolumenal tissue.

In general maintaining the cannulas in an organized fashion facilitates the proper orientation for incorporation of the contained sutures with a proximal ring. Further, this organization facilitates the proper orientation for securing of the suture material. The distal and/or proximal end of the cannula sets 730 may have numbers, colors, or codes to help identify each individual cannula and cannula set or series. A cannula set holder (not shown) may be held by hand or be mounted to a table, stand, endoscope, or to the tube of the device. The proximal graft may now be incorporated with the sutures 615 and secured as described previously.

FIGS. 24A through 24C illustrate another exemplary implant 800. Implant 800 may include at least one distal ring 805, one suspension line 810, and one impeding ball 815. The impeding ball 815 may have a through hole or bore 820 completely traversing a central axis of impeding ball 815. Impeding ball 815 may also have a bore that is located other than centrally through the ball, that is at a location above and/or below bore 820 illustrated in FIGS. 24A through 24C. One of skill in the art will appreciate that bore 820, and any additional or other optional bores, may be of varying size, although generally it is of a size that will not become easily filled with food and digestive materials. At the same time bore 820 may be large enough that if food material does enter bore 820 the food material may easily be washed out by ingested liquids. Suspension line 810 may or may not be adjustable in length, as described above.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. An endolumenal implant comprising:
   a supporting member including a central opening;
   an impeding member suspended, at least in part, below the supporting member and substantially aligned with the central opening, wherein the vertical displacement of the impeding member relative to the central opening defines an effective orifice, wherein the vertical displacement is adjustable;
   a suspension line coupled to the support member and the impending member, for suspending the impending member a predetermined distance below the support member, wherein the suspension line is endoscopically adjustable in length; and an adjustment pin rotatably disposed in the impending member.

2. The endolumenal implant of claim 1 wherein the suspension line is adjustable by rotating the adjustment pin in a predetermined direction.

3. The endolumenal implant of claim 1 wherein the supporting member comprises two ring members configured to engage endolumenal tissue therebetween to secure the endolumenal implant.

4. The endolumenal implant of claim 3 further comprising suture members configured to secure the two ring members and the endolumenal tissue.

5. The endolumenal implant of claim 1, wherein the impeding member is removable and may be added after implantation of the support member.

6. The endolumenal implant of claim 1, wherein the supporting member further comprises:

a proximal ring having a first plurality of apertures;

a distal ring having a second plurality of apertures; and a plurality of suture members corresponding to the first and second plurality of apertures;

wherein the proximal ring and distal ring are substantially aligned and configured to receive a portion of endolumenal tissue therebetween, such that the plurality of suture members pass through the first plurality of apertures, the endolumenal tissue, and the second plurality of apertures.

7. The endolumenal implant of claim 1, wherein the impeding member is spherical in shape.

8. The endolumenal implant of claim 1, wherein the impeding member comprises a predetermined amount of medication for release into a patient's body.

9. The endolumenal implant of claim 1, wherein the impeding member comprises an electrical device.

10. The endolumenal implant of claim 9, wherein the electrical device is selected from a group consisting of a PH sensing device, a temperature sensing device, an electrical stimulation device, an imaging device, a transmitting device and a memory device.

11. The endolumenal implant of claim 1, wherein the two rings are made of an elastic material.

* * * * *